United States Patent
LaPointe

(12) 
(10) Patent No.: US 6,462,156 B2
(45) Date of Patent: Oct. 8, 2002

(54) CATALYST ACTIVATORS COMPRISING EXPANDED ANIONS

(75) Inventor: Robert E. LaPointe, Midland, MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 10/097,395

(22) Filed: Mar. 13, 2002

(65) Prior Publication Data

US 2002/0132729 A1 Sep. 19, 2002

Related U.S. Application Data

(62) Division of application No. 09/823,650, filed on Apr. 2, 2001, now Pat. No. 6,395,671, which is a continuation of application No. 09/251,664, filed on Feb. 17, 1999, now abandoned.
(60) Provisional application No. 60/075,329, filed on Feb. 20, 1998.

(51) Int. Cl.$^7$ .......................... B01J 31/100; C08F 4/52; C08F 4/64
(52) U.S. Cl. ............... 526/165; 526/134; 526/160; 526/943; 502/103; 502/152; 502/164; 502/167
(58) Field of Search ................... 502/103, 152, 502/164, 167; 526/134, 160, 165, 943

(56) References Cited

U.S. PATENT DOCUMENTS

| | | | |
|---|---|---|---|
| 3,696,161 A | 10/1972 | Kobetz et al. | ............... 260/677 |
| 5,132,380 A | 7/1992 | Stevens et al. | |
| 5,153,157 A | 10/1992 | Hlatky et al. | |
| 5,189,192 A | 2/1993 | LaPointe et al. | |
| 5,198,401 A | 3/1993 | Turner et al. | |
| 5,321,106 A | 6/1994 | LaPointe | |
| 5,350,723 A | 9/1994 | Neiithamer et al. | |
| 5,407,884 A | 4/1995 | Turner et al. | |
| 5,447,895 A | 9/1995 | Marks et al. | |
| 5,470,927 A | 11/1995 | Turner et al. | |
| 5,625,087 A | 4/1997 | Devore et al. | |
| 6,124,231 A | 9/2000 | Fritze et al. | ................. 502/152 |

FOREIGN PATENT DOCUMENTS

EP 520732 6/1995

OTHER PUBLICATIONS

"Organo–Lewis Acids as Cocatalysts in Cationic Metal-locene Polymerization Catalysis. Unusual Characteristics of Sterically Encumbered Tris(perfluorobiphenyl) borane", Marks et al, J. Am. Chem. Soc., 118, pp. 12451–12452, (1996).

Christen M. Giandomenico, et al., *Journal of American Chemical Society*, 103, 1407–1412, 1981.

Primary Examiner—David W. Wu
Assistant Examiner—Caixia Lu

(57) ABSTRACT

Catalyst compositions comprising a group 4 metal complex and an activator corresponding to the formula:

$$(A^{*+a})_b(Z^*J^*_j)^{-c}{}_d,$$

wherein:

A* is a cation of charge +a, selected from the group consisting of ammonium-, sulfonium-, phosphonium-, oxonium-, carbonium-, silylium-, ferrocenium-, $Ag^+$, and $Pb^{+2}$;

Z* is an anion group of from 1 to 50 atoms, not counting hydrogen atoms, further containing two or more Lewis base sites as defined in the claims;

J* independently each occurrence is a Lewis acid coordinated to at least one Lewis base site of Z*, and optionally two or more such J* groups may be joined together in a moiety having multiple Lewis acidic functionality, j is a number from 2 to 12 and a, b, c, and d are integers from 1 to 3, with the proviso that a×b is equal to c×d.

13 Claims, No Drawings

CATALYST ACTIVATORS COMPRISING EXPANDED ANIONS

CROSS REFERENCE STATEMENT

This application is a divisional of U.S. application Ser. No. 09/823,650, filed Apr. 2, 2001, now U.S. Pat. No. 6,395,671 which is a continuation of U.S. application Ser. No. 09/251,664, filed Feb. 17, 1999, now abandoned, which claims benefit of priority from Provisional No. 60/075,329, filed Feb. 20, 1998.

BACKGROUND INFORMATION

The present invention relates to compounds that are useful as catalyst components. More particularly the present invention relates to such compounds that are particularly adapted for use in the coordination polymerization of unsaturated compounds comprising an anion containing at least two Lewis basic sites which are coordinated to Lewis acids. Such compounds are particularly advantageous for use in a polymerization process wherein catalyst, catalyst activator, and at least one polymerizable monomer are combined under polymerization conditions to form a polymeric product.

It is previously known in the art to activate Ziegler-Natta polymerization catalysts, particularly such catalysts comprising Group 3–10 metal complexes containing delocalized π-bonded ligand groups, by the use of Bronsted acid salts capable of transferring a proton to form a cationic derivative or other catalytically active derivative of such Group 3–10 metal complex. Preferred Bronsted acid salts are such compounds containing a cation/anion pair that is capable of rendering the Group 3–10 metal complex catalytically active. Suitable activators comprise fluorinated arylborate anions, such as tetrakis(pentafluorophenyl)borate. Additional suitable anions include sterically shielded diboron anions of the formula:

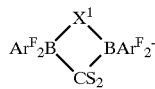

wherein: S is hydrogen, alkyl, fluoroalkyl, aryl, or fluoroaryl, $Ar^F$ is fluoroaryl, and $X^1$ is either hydrogen or halide, disclosed in U.S. Pat. No. 5,447,895. Additional examples include carborane compounds such as are disclosed and claimed in U.S. Pat. No. 5,407,884.

Examples of preferred charge separated (cation/anion pair) activators are ammonium, sulfonium, or phosphonium salts capable of transferring a hydrogen ion, disclosed in U.S. Pat. Nos. 5,198,401, 5,132,380, 5,470,927 and 5,153,157, as well as oxidizing salts such as ferrocenium, silver or lead salts, disclosed in U.S. Pat. Nos. 5,189,192 and 5,321,106 and strongly Lewis acidic salts such as carbonium or silylium salts, disclosed in U.S. Pat. Nos. 5,350,723 and 5,625,087.

Further suitable activators for the above metal complexes include strong Lewis acids including tris(perfluorophenyl) borane and tris(perfluorobiphenyl)borane. The former composition has been previously disclosed for the above stated end use in EP-A-520,732, whereas the latter composition is similarly disclosed by Marks, et al., in *J. Am. Chem. Soc.*, 118, 12451–12452 (1996). For the teachings contained therein, the foregoing patents, publications and equivalent United States applications are hereby incorporated by reference.

Despite the satisfactory performance of the foregoing catalyst activators under a variety of polymerization conditions, there is still a need for improved cocatalysts for use in the activation of various metal complexes under a variety of reaction conditions. Accordingly, it would be desirable if there were provided compounds that could be employed in solution, slurry, gas phase or high pressure polymerizations and under homogeneous or heterogeneous process conditions having improved activation properties.

SUMMARY OF THE INVENTION

According to the present invention there are now provided compounds useful as catalyst activators corresponding to the formula: $(A^{*+a})_b(Z^*J^*_j)^{-c}_d$, wherein:
  $A^*$ is a cation of charge +a,
  $Z^*$ is an anion group of from 1 to 50, preferably 1 to 30 atoms, not counting hydrogen atoms, further containing two or more Lewis base sites;
  $J^*$ independently each occurrence is a Lewis acid coordinated to at least one Lewis base site of $Z^*$, and optionally two or more such $J^*$ groups may be joined together in a moiety having multiple Lewis acidic functionality,
  j is a number from 2 to 12 and
  a, b, c, and d are integers from 1 to 3, with the proviso that a×b is equal to c×d.

Additionally according to the present invention there is provided a catalyst composition for polymerization of an ethylenically unsaturated, polymerizable monomer comprising, in combination, the above described compound and a Group 3–10 metal complex that is capable of activation to form an addition polymerization catalyst, or the reaction product of such combination.

Additionally according to the present invention there is provided a process for polymerization of one or more ethylenically unsaturated, polymerizable monomers comprising contacting the same, optionally in the presence of an inert aliphatic, alicyclic or aromatic hydrocarbon, with the above catalyst composition.

The foregoing compounds are uniquely adapted for use in activation of a variety of metal complexes, especially Group 4 metal complexes, under standard and atypical olefin polymerization conditions. Because of this fact, the foregoing compounds are capable of forming highly desirable olefin polymers in high efficiency.

DETAILED DESCRIPTION OF THE INVENTION

All references herein to elements belonging to a certain Group refer to the Periodic Table of the Elements published and copyrighted by CRC Press, Inc., 1995. Also any reference to the Group or Groups shall be to the Group or Groups as reflected in this Periodic Table of the Elements using the IUPAC system for numbering groups.

The catalyst activators of the invention are further characterized in the following manner. $A^{*+a}$ is desirably chosen to provide overall neutrality to the compound and to not interfere with subsequent catalytic activity. Moreover, the cation may participate in the formation of the active catalyst species, desirably through a proton transfer, oxidation, or ligand abstraction mechanism, or a combination thereof. Additionally, certain cations beneficially improve the solubility of the resulting activator in particular reaction media under use conditions. For example, in the homopolymerization or copolymerization of aliphatic olefins, particularly in the solution phase, an aliphatic diluent is commonly used. Accordingly, cationic species that are relatively soluble in such reaction media, or render the catalyst activator more soluble therein are highly preferred.

Examples of suitable cations include ammonium, sulfonium, phosphonium, oxonium, carbonium, and sylylium cations, preferably those containing up to 80 atoms not counting hydrogen, as well as ferrocenium, Ag+, Pb+2, or similar oxidizing cations. In a preferred embodiment, a, b, c and d are all equal to one.

Z* can be any anionic moiety containing two or more Lewis basic sites. Preferably, the Lewis base sites are on different atoms of a polyatomic anionic moiety. Desirably, such Lewis basic sites are relatively sterically accessible to the Lewis acid, J*. Preferably the Lewis basic sites are on nitrogen or carbon atoms. Examples of suitable Z* anions include cyanide, azide, amide and substituted amide, amidinide and substituted amidinide, dicyanamide, imidazolide, substituted imidazolide, imidazolinide, substituted imidazolinide, tricyanomethide, tetracycanoborate, puride, squarate, 1,2,3-triazolide, substituted 1,2,3-triazolide, 1,2,4-triazolide, substituted 1,2,4-triazolide, pyrimidinide, substituted pyrimidinide, tetraimidazoylborate and substituted tetraimidazoylborate anions, wherein each substituent, if present, is a halo, hydrocarbyl, halohydrocarbyl, silyl, (including mono-, di- and tri(hydrocarbyl)silyl), silylhydrocarbyl, or halocarbyl group of up to 20 atoms not counting hydrogen, or two such substituents together form a saturated or unsaturated ring system.

Preferred Z* groups are: imidazolide, 2-nonadecylimidazolide, 2-undecylimidazolide, 2-tridecylimidazolide, 2-pentadecylimidazolide, 2-heptadecylimidazolide, 2-nonadecylimidazolide, 4,5-difluoroimidazolide, 4,5-dichloroimidazolide, 4,5-dibromoimidazolide, 4,5-bis(heptadecyl)imidazolide, 4,5-bis(undecyl)imidazolide, imidazolinide, 2-nonadecylimidazolinide, 2-undecylimidazolinide, 2-tridecylimidazolinide, 2-pentadecylimidazolinide, 2-heptadecylimidazolinide, 2-nonadecylimidazolinide, 4,5-difluoroimidazolinide, 4,5-dichloroimidazolinide, 4,5-dibromoimidazolinide, 4,5-bis(heptadecyl)imidazolinide, 4,5-bis(undecyl)imidazolinide, didecylamide, piperidinide, 4,4-dimethylimidazolinide, tetra-5-pyrimidinylborate, pyrimidinide, 5,6-dichlorobenzimidazolide, 4,5-dicyanoimidazolide, and 5,6-dimethylbenzimidazolide anions.

Coordinated to the Lewis base sites of the anion are from 2 to 12 Lewis acids, J*, two or more of which may be joined together in a moiety having multiple Lewis acidic functionality. Preferably, from 2 to 4 J* groups having from 3 to 100 atoms not counting hydrogen are present.

More specific examples of the foregoing Lewis acid compounds, J*, correspond to the formula:

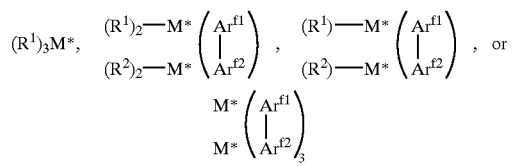

wherein:
M* is aluminum or boron;
R¹ and R² independently each occurrence are hydride, halide, or a hydrocarbyl, halocarbyl, halohydrocarbyl, dialkylamido, alkoxide, or aryloxide group of up to 20 carbons, with the proviso that in not more than one occurrence is R¹ or R² halide, and Ar^{f1}–Ar^{f2} in combination, independently each occurrence, is a divalent fluoro-substituted aromatic group of from 6 to 20 carbons.

Highly preferred Lewis acids are aluminum or boron compounds corresponding to the formula: AlR¹₃, or BR¹₃, wherein R¹ independently each occurrence is selected from hydrocarbyl, halocarbyl, and halohydrocarbyl radicals, said R¹ having up to 20 carbons. In a more highly preferred embodiment, R¹ is a fluorinated $C_{1-20}$ hydrocarbyl group, most preferably, a fluorinated aryl group, especially, pentafluorophenyl.

Preferred examples of the foregoing Lewis acid groups containing multiple Lewis acid sites are:

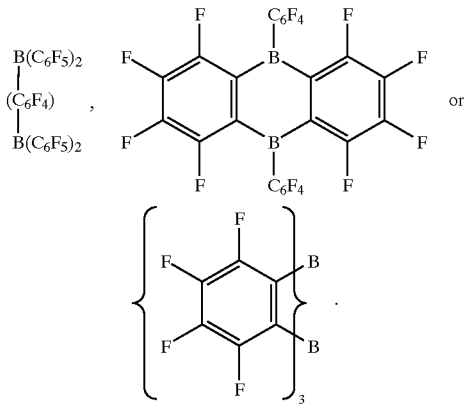

Suitable expanded anion compounds according to the present invention include the ammonium, phosphonium, sulfonium, oxonium, carbonium, silylium, lead (II), silver or ferrocenium salts of: bis(tris(pentafluorophenyl)borane) cyanide, bis(tris(pentafluorophenyl)borane)azide, bis(tris (pentafluorophenyl)borane)dicyanamide, bis(tris (pentafluorophenyl)borane)imidazolide, bis(tris (pentafluorophenyl)borane)- 2-undecylimidazolide, bis(tris (pentafluorophenyl)borane)imidazolinide, bis(tris (pentafluorophenyl)borane)-2-undecylimidazolinide, bis (tris(pentafluorophenyl)borane)-5,6-dimethylbenzimidazolide, bis(tris(pentafluorophenyl) borane)-4,5-bis(heptadecyl)imidazolide, tris(tris (pentafluoro-phenyl)boranetricyanomethide, tris(tris (pentafluorophenyl)borane)puride, tetrakis(tris (pentafluorophenyl)borane)tetraimidazoylborate, bis(tris (pentafluorophenyl)alumane)cyanide, bis(tris (pentafluorophenyl)alumane)azide, bis(tris (pentafluorophenyl)alumane)dicyanamide, bis(tris (pentafluorophenyl)alumane)imidazolide, bis(tris (pentafluorophenyl)alumane)-2-undecylimidazolide, bis(tris (pentafluorophenyl)alumane)imidazolinide, bis(tris (pentafluorophenyl)alumane)-2-undecylimidazolinide, bis (tris(pentafluorophenyl)alumane)-5,6-dimethylbenzimidazolide, bis(tris(pentafluorophenyl) alumane)-4,5-bis(heptadecyl)imidazolide, tris(tris (pentafluoro-phenyl)alumanetricyanomethide, tris(tris (pentafluorophenyl)alumane)puride, tetrakis(tris (pentafluorophenyl)alumane)tetraimidazoylborate, bis(tris (heptafluoro-2-naphthyl)borane)cyanide, bis(tris (heptafluoro-2-naphthyl)borane)azide, bis(tris(heptafluoro-2-naphthyl)borane)dicyanamide, bis(tris(heptafluoro-2-naphthyl)borane)imidazolide, bis(tris(heptafluoro-2-naphthyl)borane)-2-undecylimidazolide, bis(tris (heptafluoro-2-naphthyl)borane)-5,6-dimethylbenzimidazolide, bis(tris(heptafluoro-2-naphthyl)borane)-4,5-bis(heptadecyl)imidazolide, tris(tris(heptafluoro-2-naphthyl)boranetricyanomethide, tris(tris(heptafluoro-2-naphthyl)borane)puride, tetrakis(tris(heptafluoro-2-naphthyl)borane)tetraimidazoylborate, bis(tris(heptafluoro-2-naphthyl)alumane)cyanide, bis(tris(heptafluoro-2-naphthyl)alumane)azide, bis(tris(heptafluoro-2-naphthyl)alumane)dicyanamide, bis(tris(heptafluoro-2-naphthyl)alumane)imidazolide, bis(tris(heptafluoro-2-naphthyl)alumane)-2-undecylimidazolide, bis(tris(heptafluoro-2-naphthyl)alumane)-5,6-dimethylbenzimidazolide, bis(tris(heptafluoro-2-naphthyl)alumane)-4,5-bis(heptadecyl)imidazolide, tris(trisheptafluoro-2-naphthyl)alumanetricyanomethide, tris(tris(heptafluoro-2-naphthyl)alumane)puride, and tetrakis(tris(heptafluoro-2-naphthyl)alumane)tetraimidazoylborate.

Examples of suitable expanded anion compounds are the foregoing ammonium salts, especially those which comprise trihydrocarbyl-substituted ammonium cations, especially trimethylammonium-, triethylammonium-, tripropylammonium-, tri(n-butyl)ammonium-, methyldi(octadecyl)ammonium-, methyidi(tetradecyl)ammonium-, methyl(tetradecyl)(octadecyl)ammonium-, N,N-dimethylanilinium-, N,N-diethylanilinium-, N,N-dimethyl(2,4,6-trimethylanilinium)-, and methyidicyclohexylammonium-cations or mixtures thereof.

Most preferred ammonium cation containing salts are those containing trihydrocarbyl-substituted ammonium cations containing one or two $C_{10}$–$C_{40}$ alkyl groups, especially methylbis(octadecyl)ammonium- and methylbis(tetradecyl)ammoniumcations. It is further understood that the cation may comprise a mixture of hydrocarbyl groups of differing lengths. For example, the protonated ammonium-cation derived from the commercially available long chain amine comprising a mixture of two $C_{14}$, $C_{16}$ or $C_{18}$ alkyl groups and one methyl group. Such amines are available from Witco Corp., under the trade name Kemamine™ T9701, and from Akzo-Nobel under the trade name Armeen™ M2HT.

The foregoing cocatalysts (illustrated by those having imidazolide, substituted imidazolide, imidazolinide, substituted imidazolinide, benzimidazolide, or substituted benzimidazolide anions) may be depicted schematically as follows:

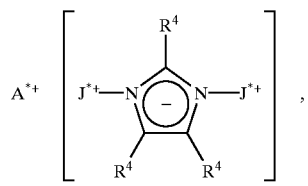

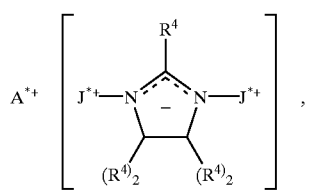

-continued

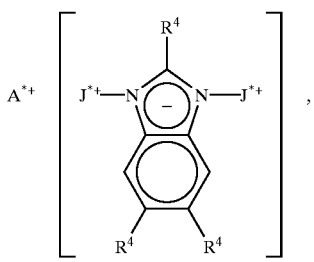

wherein:
  $A^{*+}$ is a monovalent cation as previously defined, and preferably is a trihydrocarbyl ammonium cation, containing one or two $C_{10-40}$ alkyl groups, especially the methylbis(tetradecyl)ammonium- or methylbis(octadecyl)ammonium-cation, $R^4$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and $J^{*'}$ is tris(pentafluorophenyl)borane or tris(pentafluorophenyl)alumane).

Examples of the most highly preferred catalyst activators herein include the forgoing trihydrocarbylammonium-, especially, methylbis(tetradecyl)ammonium- or methylbis(octadecyl)ammonium-salts of:

bis(tris(pentafluorophenyl)borane)imidazolide,
bis(tris(pentafluorophenyl)borane)-2-undecylimidazolide,
bis(tris(pentafluorophenyl)borane)-2-heptadecylimidazolide,
bis(tris(pentafluorophenyl)borane)-4,5-bis(undecyl)imidazolide,
bis(tris(pentafluorophenyl)borane)-4,5-bis(heptadecyl)imidazolide,
bis(tris(pentafluorophenyl)borane)imidazolinide,
bis(tris(pentafluorophenyl)borane)-2-undecylimidazolinide,
bis(tris(pentafluorophenyl)borane)-2-heptadecylimidazolinide,
bis(tris(pentafluorophenyl)borane)-4,5-bis(undecyl)imidazolinide,
bis(tris(pentafluorophenyl)borane)-4,5-bis(heptadecyl)imidazolinide,
bis(tris(pentafluorophenyl)borane)-5,6-dimethylbenzimidazolide,
bis(tris(pentafluorophenyl)borane)-5,6-bis(undecyl)benzimidazolide,
bis(tris(pentafluorophenyl)alumane)imidazolide,
bis(tris(pentafluorophenyl)alumane)-2-undecylimidazolide,
bis(tris(pentafluorophenyl)alumane)-2-heptadecylimidazolide,
bis(tris(pentafluorophenyl)alumane)-4,5-bis(undecyl)imidazolide,
bis(tris(pentafluorophenyl)alumane)-4,5-bis(heptadecyl)imidazolide,
bis(tris(pentafluorophenyl)alumane)imidazolinide, bis(tris(pentafluorophenyl)alumane)-2-undecylimidazolinide, bis(tris(pentafluorophenyl)alumane)-2-heptadecylimidazolinide, bis(tris(pentafluorophenyl)alumane)-4,5-bis(undecyl)imidazolinide, bis(tris(pentafluorophenyl)alumane)-4,5-bis(heptadecyl)imidazolinide, bis(tris(pentafluorophenyl)alumane)-5,6-dimethylbenzimidazolide, and bis(tris(pentafluorophenyl)alumane)-5,6-bis(undecyl)benzimidazolide.

The compounds may be prepared by a condensation reaction between the alkali metal salt of the anion, Z*, and a Lewis acid, J*, preferably under phase transfer conditions, using for example a crown ether to solubilize the alkali metal salt, followed by a metathesis reaction with the corresponding halide salt of the cation, $A^{*+a}$. Certain of the cocatalysts are also amenable to preparation via a one step, single reactor process. For example, the ammonium or phosphonium imidiazolide, or substituted imidiazolide salts can be prepared by contacting the Lewis acid, J*, or its Lewis base adduct, such as an etherate, with the neutral compound corresponding to the anion, Z*. Both reactants are desirably relatively lipophilic, such that the reaction can be performed in non-polar solvents. Addition of the free base corresponding to the cation, $A^{*+a}$, results in formation of the charge separated species, which may be recovered from the reaction mixture by devolatilization or used without further purification.

Suitable catalysts for use in combination with the foregoing cocatalysts include any compound or complex of a metal of Groups 3–10 of the Periodic Table of the Elements capable of being activated to polymerize ethylenically unsaturated compounds by the present activators. Examples include Group 10 diimine derivatives corresponding to the formula:

wherein

M* is Ni(II) or Pd(II);

K is halo, hydrocarbyl, or hydrocarbyloxy;

and the two nitrogen atoms are linked by a bridging system.

Such catalysts have been previously disclosed in *J. Am. Chem. Soc.*, 118, 267–268 (1996), *J. Am. Chem. Soc.*, 117, 6414–6415 (1995), and *Organometallics*, 16, 1514–1516, (1997).

Additional catalysts include derivatives of Group 3, 4, or Lanthanide metals which are in the +2, +3, or +4 formal oxidation state. Preferred compounds include metal complexes containing from 1 to 3 π-bonded anionic or neutral ligand groups, which may be cyclic or non-cyclic delocalized π-bonded anionic ligand groups. Exemplary of such π-bonded anionic ligand groups are conjugated or nonconjugated, cyclic or non-cyclic dienyl groups, allyl groups, boratabenzene groups, phosphole, and arene groups. By the term "π-bonded" is meant that the ligand group is bonded to the transition metal by a sharing of electrons from a partially delocalized π-bond.

Each atom in the delocalized π-bonded group may independently be substituted with a radical selected from the group consisting of hydrogen, halogen, hydrocarbyl, halohydrocarbyl, hydrocarbyl-substituted metalloid radicals wherein the metalloid is selected from Group 14 of the Periodic Table of the Elements, and such hydrocarbyl- or hydrocarbyl-substituted metalloid radicals further substituted with a Group 15 or 16 hetero atom containing moiety. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. In addition two or more such radicals may together form a fused ring system, including partially or fully hydrogenated fused ring systems, or they may form a metallocycle with the metal. Suitable hydrocarbyl-substituted organometalloid radicals include mono-, di- and tri-substituted organometalloid radicals of Group 14 elements wherein each of the hydrocarbyl groups contains from 1 to 20 carbon atoms. Examples of suitable hydrocarbyl-substituted organometalloid radicals include trimethylsilyl, triethylsilyl, ethyldimethylsilyl, methyldiethylsilyl, triphenylgermyl, and trimethylgermyl groups. Examples of Group 15 or 16 hetero atom containing moieties include amine, phosphine, ether or thioether moieties or divalent derivatives thereof, e.g. amide, phosphide, ether or thioether groups bonded to the transition metal or Lanthanide metal, and bonded to the hydrocarbyl group or to the hydrocarbyl-substituted metalloid containing group.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, phosphole, and boratabenzene groups, as well as hydrocarbyl-silyl-(including mono-, di-, or tri(hydrocarbyl) silyl) substituted derivatives thereof. Preferred anionic, delocalized π-bonded groups are cyclopentadienyl, pentamethylcyclopentadienyl, tetramethylcyclopentadienyl, tetramethyl(trimethylsilyl)-cyclopentadienyl, indenyl, 2,3-dimethylindenyl, fluorenyl, 2-methylindenyl, 2-methyl-4-phenylindenyl, tetrahydrofluorenyl, octahydrofluorenyl, and tetrahydroindenyl.

The boratabenzenes are anionic ligands that are boron containing analogues to benzene. They are previously known in the art having been described by G. Herberich, et al., in *Organometallics*, 14,1, 471–480 (1995). Preferred boratabenzenes correspond to the formula:

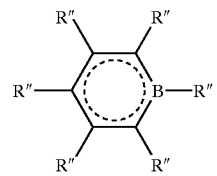

wherein R" is selected from the group consisting of hydrocarbyl, silyl, N,N-dihydrocarbylamino, or germyl, said R" having up to 20 non-hydrogen atoms. In complexes involving divalent derivatives of such delocalized π-bonded groups one atom thereof is bonded by means of a covalent bond or a covalently bonded divalent group to another atom of the complex thereby forming a bridged system.

Phospholes are anionic ligands that are phosphorus containing analogues to a cyclopentadienyl group. They are previously known in the art having been described by WO 98/50392, and elsewhere. Preferred phosphole ligands correspond to the formula:

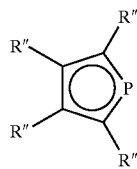

wherein R" is selected from the group consisting of hydrocarbyl, silyl, N,N-dihydrocarbylamino, or germyl, said R" having up to 20 non-hydrogen atoms, and optionally one or more R" groups may be bonded together forming a multicyclic fused ring system, or form a bridging group connected to the metal. In complexes involving divalent derivatives of such delocalized π-bonded groups one atom thereof is bonded by means of a covalent bond or a covalently bonded divalent group to another atom of the complex thereby forming a bridged system.

Phosphinimine/cyclopentadienyl complexes are disclosed in EP-A-890581 and correspond to the formula $$[(R^{})_3-P=N]_b M^{}(Cp)(L^1)_{3-b},$$

wherein:
R is a monovalent ligand, illustrated by hydrogen, halogen, or hydrocarbyl, or two R groups together form a divalent ligand,
M** is a Group 4 metal,
Cp is cyclopentadienyl, or similar delocalized π-bonded group,
$L^1$ is a monovalent ligand group, illustrated by hydrogen, halogen or hydrocarbyl, and
n is 1 or 2.

A suitable class of catalysts are transition metal complexes corresponding to the formula:

$$Lp_l MX_m X'_n X''_p,$$

or a dimer thereof
wherein:
Lp is an anionic, delocalized, π-bonded group that is bound to M, containing up to 50 non-hydrogen atoms, optionally two Lp groups may be joined together forming a bridged structure, and further optionally one Lp may be bound to X;
M is a metal of Group 4 of the Periodic Table of the Elements in the +2, +3 or +4 formal oxidation state;
X is an optional, divalent substituent of up to 50 non-hydrogen atoms that together with Lp forms a metallocycle with M;
X' is an optional neutral ligand having up to 20 non-hydrogen atoms;
X" each occurrence is a monovalent, anionic moiety having up to 40 non-hydrogen atoms, optionally, two X" groups may be covalently bound together forming a divalent dianionic moiety having both valences bound to M, or, optionally 2 X" groups may be covalently bound together to form a neutral, conjugated or nonconjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;
l is 0, 1 or 2;
m is 0 or 1;
n is a number from 0 to 3;
p is an integer from 0 to 3; and
the sum, l+m+p, is equal to the formal oxidation state of M, except when 2 X" groups together form a neutral conjugated or non-conjugated diene that is π-bonded to M, in which case the sum l+m is equal to the formal oxidation state of M.

Preferred complexes include those containing either one or two Lp groups. The latter complexes include those containing a bridging group linking the two Lp groups. Preferred bridging groups are those corresponding to the formula $(ER^*_2)_x$ wherein E is silicon, germanium, tin, or carbon, R* independently each occurrence is hydrogen or a group selected from silyl, hydrocarbyl, hydrocarbyloxy and combinations thereof, said R* having up to 30 carbon or silicon atoms, and x is 1 to 8. Preferably, R* independently each occurrence is methyl, ethyl, propyl, benzyl, tert-butyl, phenyl, methoxy, ethoxy or phenoxy.

Examples of the complexes containing two Lp groups are compounds corresponding to the formula:

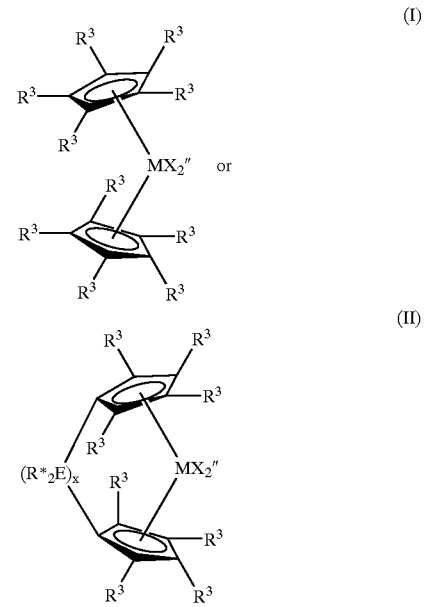

wherein:
M is titanium, zirconium or hafnium, preferably zirconium or hafnium, in the +2 or +4 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, and
X" independently each occurrence is an anionic ligand group of up to 40 non-hydrogen atoms, or two X" groups together form a divalent anionic ligand group of up to non-hydrogen atoms or together are a conjugated diene having from 4 to 30 non-hydrogen atoms forming a π-complex with M, whereupon M is in the +2 formal oxidation state, and
R*, E and x are as previously defined.

The foregoing metal complexes are especially suited for the preparation of polymers having stereoregular molecular structure. In such capacity it is preferred that the complex possesses $C_s$ symmetry or possesses a chiral, stereorigid structure. Examples of the first type are compounds possessing different delocalized π-bonded systems, such as one cyclopentadienyl group and one fluorenyl group. Similar systems based on Ti(IV) or Zr(IV) were disclosed for preparation of syndiotactic olefin polymers in Ewen, et al., *J. Am. Chem. Soc.* 110, 6255–6256 (1980). Examples of chiral structures include rac bis-indenyl complexes. Similar systems based on Ti(IV) or Zr(IV) were disclosed for preparation of isotactic olefin polymers in Wild et al., *J. Organomet. Chem.*, 232, 233–47, (1982).

Exemplary bridged ligands containing two π-bonded groups are: dimethylbis(cyclopentadienyl)silane, dimethylbis(tetramethylcyclopentadienyl)silane, dimethylbis(2-ethylcyclopentadien-1-yl)silane, dimethylbis(2-t-butylcyclopentadien-1-yl)silane, 2,2-bis (tetramethylcyclopentadienyl)propane, dimethylbis(inden-1-yl)silane, dimethylbis(tetrahydroinden-1-yl)silane, dimethylbis(fluoren-1-yl)silane, dimethylbis(tetrahydrofluoren-1-yl)silane, dimethylbis(2-methyl-4-phenylinden-1-yl)-silane, dimethylbis(2-methylinden-1-yl) silane, dimethyl(cyclopentadienyl)(fluoren-1-yl)silane, dimethyl(cyclopentadienyl)(octahydrofluoren-1-yl)silane, dimethyl(cyclopentadienyl)(tetrahydrofluoren-1-yl)silane, (1,1,2,2-tetramethy)-1,2-bis(cyclopentadienyl)disilane, (1,2-bis(cyclopentadienyl)ethane, and dimethyl (cyclopentadienyl)-1-(fluoren-1-yl)methane.

Preferred X" groups are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Most preferred X" groups are $C_{1-20}$ hydrocarbyl groups.

A further class of metal complexes utilized in the present invention corresponds to the preceding formula $Lp_lMX_mX'_nX''_p$, or a dimer thereof, wherein X is a divalent substituent of up to 50 non-hydrogen atoms that together with Lp forms a metallocycle with M.

Preferred divalent X substituents include groups containing up to 30 non-hydrogen atoms comprising at least one atom that is oxygen, sulfur, boron or a member of Group 14 of the Periodic Table of the Elements directly attached to the delocalized π-bonded group, and a different atom, selected from the group consisting of nitrogen, phosphorus, oxygen or sulfur that is covalently bonded to M.

A preferred class of such Group 4 metal coordination complexes used according to the present invention corresponds to the formula:

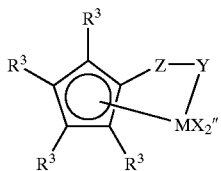

wherein:
M is titanium or zirconium, preferably titanium in the +2, +3, or +4 formal oxidation state;
$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system,
each X" is a halo, hydrocarbyl, hydrocarbyloxy or silyl group, said group having up to 20 non-hydrogen atoms, or two X" groups together form a neutral $C_{5-30}$ conjugated diene or a divalent derivative thereof;
Y is —O—, —S—, —NR*—, —PR*—; and
Z is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$, wherein R* is as previously defined.

Illustrative Group 4 metal complexes that may be employed in the practice of the present invention include:
cyclopentadienyltitaniumtrimethyl,
cyclopentadienyltitaniumtriethyl,
cyclopentadienyltitaniumtriisopropyl,
cyclopentadienyltitaniumtriphenyl,
cyclopentadienyltitaniumtribenzyl,
cyclopentadienyltitanium-2,4-dimethylpentadienyl,
cyclopentadienyltitanium-2,4-dimethylpentadienyl.triethylphosphine,
cyclopentadienyltitanium-2,4-dimethylpentadienyl.trimethylphosphine,
cyclopentadienyltitaniumdimethylmethoxide,
cyclopentadienyltitaniumdimethylchloride,
pentamethylcyclopentadienyltitaniumtrimethyl,
indenyltitaniumtrimethyl,
indenyltitaniumtriethyl,
indenyltitaniumtripropyl,
indenyltitaniumtriphenyl,
tetrahydroindenyltitaniumtribenzyl,
pentamethylcyclopentadienyltitaniumtriisopropyl,
pentamethylcyclopentadienyltitaniumtribenzyl,
pentamethylcyclopentadienyltitaniumdimethylmethoxide,
pentamethylcyclopentadienyltitaniumdimethylchloride,
bis($\eta^5$-2,4-dimethylpentadienyl)titanium,
bis($\eta^5$-2,4-dimethylpentadienyl)titanium.trimethylphosphine,
bis($\eta^5$-2,4-dimethylpentadienyl)titanium.triethylphosphine,
octahydrofluorenyltitaniumtrimethyl,
tetrahydroindenyltitaniumtrimethyl,
tetrahydrofluorenyltitaniumtrimethyl,
(tert-butylamido)(1,1-dimethyl-2,3,4,9,10-η-1,4,5,6,7,8-hexahydronaphthalenyl) dimethylsilanetitaniumdimethyl,
(tert-butylamido)(1,1,2,3-tetramethyl-2,3,4,9,10-η-1,4,5, 6,7,8-hexahydronaphthalenyl) dimethylsilanetitaniumdimethyl,
(tert-butylamido)(tetramethyl-$\eta^5$-cyclopentadienyl) dimethylsilanetitanium dibenzyl,
(tert-butylamido)(tetramethyl-$\eta^5$-clopentadienyl) dimethylsilanetitanium dimethyl,
(tert-butylamido)(tetramethyl-$\eta^5$-cyclopentadienyl)-1,2-ethanediyltitanium dimethyl,
(tert-butylamido)(tetramethyl-$\eta^5$-indenyl) dimethylsilanetitanium dimethyl,
(tert-butylamido)(tetramethyl-$n^5$-cyclopentadienyl) dimethylsilane titanium (III) 2-(dimethylamino)benzyl;
(tert-butylamido)(tetramethyl-$\eta^5$-cyclopentadienyl) dimethylsilanetitanium (III) allyl, (tert-butylamido)(tetramethyl-η⁵-cyclopentadienyl) dimethylsilanetitanium (III) 2,4-dimethylpentadienyl, (tert-butylamido)(tetramethyl-η⁵-cyclopentadienyl) dimethylsilanetitanium (II) 1,4-diphenyl-1,3-butadiene, (tert-butylamido)(tetramethyl-η⁵-cyclopentadienyl) dimethylsilanetitanium (II) 1,3-pentadiene, (tert-butylamido)(2-methylindenyl) dimethylsilanetitanium (II) 1,4-diphenyl-1,3-butadiene, (tert-butylamido)(2-methylindenyl) dimethylsilanetitanium (II) 2,4-hexadiene, (tert-butylamido)(2-methylindenyl) dimethylsilanetitanium (IV) 2,3-dimethyl-1,3-butadiene, (tert-butylamido)(2-methylindenyl) dimethylsilanetitanium (IV) isoprene, (tert-butylamido)(2-methylindenyl) dimethylsilanetitanium (IV) 1,3-butadiene, (tert-butylamido)(2,3-dimethylindenyl) dimethylsilanetitanium (IV) 2,3-dimethyl-1,3-butadiene, (tert-butylamido)(2,3-dimethylindenyl) dimethylsilanetitanium (IV) isoprene (tert-butylamido)(2,3-dimethylindenyl) dimethylsilanetitanium (IV) dimethyl (tert-butylamido)(2,3-dimethylindenyl) dimethylsilanetitanium (IV) dibenzyl (tert-butylamido)(2,3-dimethylindenyl) dimethylsilanetitanium (IV) 1,3-butadiene, (tert-butylamido)(2,3-dimethylindenyl) dimethylsilanetitanium (II) 1,3-pentadiene, (tert-butylamido)(2,3-dimethylindenyl) dimethylsilanetitanium (II) 1,4-diphenyl-1,3-butadiene, (tert-butylamido)(2-methylindenyl) dimethylsilanetitanium (II) 1,3-pentadiene, (tert-butylamido)(2-methylindenyl) dimethylsilanetitanium (IV) dimethyl, (tert-butylamido)(2-methylindenyl) dimethylsilanetitanium (IV) dibenzyl, (tert-butylamido)(2-methyl-4-phenylindenyl) dimethylsilanetitanium (II) 1,4-diphenyl-1,3-butadiene, (tert-butylamido)(2-methyl-4-phenylindenyl) dimethylsilanetitanium (II) 1,3-pentadiene, (tert-butylamido)(2-methyl-4-phenylindenyl) dimethylsilanetitanium (II) 2,4-hexadiene, (tert-butylamido)(tetramethyl-η⁵-cyclopentadienyl) dimethyl-silanetitanium (IV) 1,3-butadiene, (tert-butylamido)(tetramethyl-η⁵-cyclopentadienyl) dimethylsilanetitanium (IV) 2,3-dimethyl-1,3-butadiene, (tert-butylamido)(tetramethyl-η⁵-cyclopentadienyl) dimethylsilanetitanium (IV) isoprene, (tert-butylamido)(tetramethyl-η⁵-cyclopentadienyl) dimethyl-silanetitanium (II) 1,4-dibenzyl-1,3-butadiene, (tert-butylamido)(tetramethyl-η⁵-cyclopentadienyl) dimethylsilanetitanium (II) 2,4-hexadiene, (tert-butylamido)(tetramethyl-η⁵-cyclopentadienyl) dimethyl-silanetitanium (II) 3-methyl-1,3-pentadiene, (tert-butylamido)(2,4-dimethylpentadien-3-yl) dimethylsilanetitaniumdimethyl, (tert-butylamido)(6,6-dimethylcyclohexadienyl) dimethylsilanetitaniumdimethyl, ( tert-butylamido)(1,1-dimethyl-2,3,4,9,10-η-1,4,5,6,7,8-hexahydronaphthalen-4-yl) dimethylsilanetitaniumdimethyl, (tert-butylamido)(1,1,2,3-tetramethyl-2,3,4,9,10-η-1,4,5,6,7,8-hexahydronaphthalen-4-yl) dimethylsilanetitaniumdimethyl (tert-butylamido)(tetramethyl-η⁵-cyclopentadienyl methylphenylsilanetitanium (IV) dimethyl, (tert-butylamido)(tetramethyl-η⁵-cyclopentadienyl methylphenylsilanetitanium (II) 1,4-diphenyl-1,3-butadiene, 1-(tert-butylamido)-2-(tetramethyl-η⁵-cyclopentadienyl) ethanediyltitanium (IV) dimethyl, 1-(tert-butylamido)-2-(tetramethyl-η⁵-cyclopentadienyl) ethanediyl-titanium (11) 1,4-diphenyl-1,3-butadiene, (tert-butylamido)(3-(N-pyrrolidinyl)indenyl) dimethylsilanetitanium (IV) 2,3-dimethyl-1,3-butadiene, (tert-butylamido)(3-(N-pyrrolidinyl)indenyl) dimethylsilanetitanium (IV) isoprene (tert-butylamido)(3-(N-pyrrolidinyl)indenyl) dimethylsilanetitanium (IV) dimethyl (tert-butylamido)(3-(N-pyrrolidinyl)indenyl) dimethylsilanetitanium (IV) dibenzyl (tert-butylamido)(3-(N-pyrrolidinyl)indenyl) dimethylsilanetitanium (IV) 1,3-butadiene, (tert-butylamido)(3-(N-pyrrolidinyl)indenyl) dimethylsilanetitanium (II) 1,3-pentadiene, (tert-butylamido)(3-(N-pyrrolidinyl)indenyl) dimethylsilanetitanium (II) 1,4-diphenyl-1,3-butadiene, and (tert-butylamido)(3-N-pyridinylindenyl) dimethylsilanetitanium (II) 2,4-hexadiene.

Complexes containing two Lp groups including bridged complexes suitable for use in the present invention include:

bis(cyclopentadienyl)zirconiumdimethyl,
bis(cyclopentadienyl)zirconium dibenzyl,
bis(cyclopentadienyl)zirconium methyl benzyl,
bis(cyclopentadienyl)zirconium methyl phenyl,
bis(cyclopentadienyl)zirconiumdiphenyl,
bis(cyclopentadienyl)titanium-allyl,
bis(cyclopentadienyl)zirconiummethylmethoxide,
bis(cyclopentadienyl)zirconiummethylchloride,
bis(pentamethylcyclopentadienyl)zirconiumdimethyl,
bis(pentamethylcyclopentadienyl)titaniumdimethyl,
bis(indenyl)zirconiumdimethyl,
indenylfluorenylzirconiumdimethyl,
bis(indenyl)zirconiummethyl(2-(dimethylamino)benzyl),
bis(indenyl)zirconiummethyltrimethylsilyl,
bis(tetrahydroindenyl)zirconiummethyltrimethylsilyl,
bis(pentamethylcyclopentadienyl) zirconiummethylbenzyl,
bis(pentamethylcyclopentadienyl)zirconiumdibenzyl,
bis(pentamethylcyclopentadienyl) zirconiummethylmethoxide,
bis(pentamethylcyclopentadienyl) zirconiummethylchloride, bis(methylethylcyclopentadienyl)zirconiumdimethyl,
bis(butylcyclopentadienyl)zirconiumdibenzyl,
bis(t-butylcyclopentadienyl)zirconiumdimethyl,
bis(ethyltetramethylcyclopentadienyl) zirconiumdimethyl,
bis(methylpropylcyclopentadienyl)zirconiumdibenzyl,
bis(trimethylsilylcyclopentadienyl)zirconiumdibenzyl,
dimethylsilyl-bis(cyclopentadienyl)zirconiumdimethyl,
dimethylsilyl-bis(tetramethylcyclopentadienyl)titanium (III) allyl
dimethylsilyl-bis(t-butylcyclopentadienyl) zirconiumdichloride,
dimethylsilyl-bis(n-butylcyclopentadienyl) zirconiumdichloride,
(methylene-bis(tetramethylcyclopentadienyl)titanium (III) 2-(dimethylamino)benzyl,
(methylene-bis(n-butylcyclopentadienyl)titanium(III) 2-(dimethylamino)benzyl,
dimethylsilyl-bis(indenyl)zirconiumbenzylchloride,
dimethylsilyl-bis(2-methylindenyl)zirconiumdimethyl,
dimethylsilyl-bis(2-methyl-4-phenylindenyl) zirconiumdimethyl,
dimethylsilyl-bis(2-methylindenyl)zirconium-1,4-diphenyl-1,3-butadiene,
dimethylsilyl-bis(2-methyl-4-phenylindenyl)zirconium (II) 1,4-diphenyl-1,3-butadiene,
dimethylsilyl-bis(tetrahydroindenyl)zirconium(II) 1,4-diphenyl-1,3-butadiene,
dimethylsilyl-bis(fluorenyl)zirconiummethylchloride,
dimethylsilyl-bis(tetrahydrofluorenyl)zirconium bis (trimethylsilyl),
(isopropylidene)(cyclopentadienyl)(fluorenyl) zirconiumdibenzyl, and
dimethylsilyl(tetramethylcyclopentadienyl)(fluorenyl) zirconium dimethyl.

Other catalysts, especially catalysts containing other Group 4 metals, will, of course, be apparent to those skilled in the art. Most highly preferred metal complexes for use herein are the following metal complexes:

(t-butylamido)dimethyl(tetramethylcyclopentadienyl) silanetitanium dimethyl,
(t-butylamido)dimethyl(tetramethylcyclopentadienyl) silanetitanium (II) 1,3-pentadiene,
(t-butylamido)dimethyl(tetramethylcyclopentadienyl) silanetitanium (II) 1,4diphenyl-1,3-butadiene,
(cyclohexylamido)dimethyl (tetramethylcyclopentadienyl)silanetitanium dimethyl,
cyclohexylamido)dimethyl(tetramethylcyclopentadienyl) silanetitanium (II) 1,3-pentadiene,
cyclohexylamido)dimethyl(tetramethylcyclopentadienyl) silanetitanium (II) 1,4diphenyl-1,3-butadiene,
(cyclododecylamido)dimethyl (tetramethylcyclopentadienyl)silanetitanium dimethyl,
(cyclododecylamido)dimethyl (tetramethylcyclopentadienyl)silanetitanium (II) 1,3-pentadiene,
(cyclododecylamido)dimethyl (tetramethylcyclopentadienyl)silanetitanium (II) 1,4 diphenyl-1,3-butadiene,
(t-butylamido)dimethyl(2-methyl-s-indacen-1-yl) silanetitanium dimethyl,
(t-butylamido)dimethyl(2-methyl-s-indacen-1-yl) silanetitanium (II) 1,3-pentadiene,
(t-butylamido)dimethyl(2-methyl-s-indacen-1-yl) silanetitanium (II) 1,4 diphenyl-1,3-butadiene,
(cyclohexylamido)dimethyl(2-methyl-s-indacen-1-yl) silanetitanium dimethyl,
cyclohexylamido)dimethyl(2-methyl-s-indacen-1-yl) silanetitanium (II) 1,3-pentadiene,
cyclohexylamido)dimethyl(2-methyl-s-indacen-1-yl) silanetitanium(II) 1,4 diphenyl-1,3-butadiene,
(cyclododecylamido)dimethyl(2-methyl-s-indacen-1-yl) silanetitanium dimethyl,
(cyclododecylamido)dimethyl(2-methyl-s-indacen-1-yl) silanetitanium(II) 1,3-pentadiene,
(cyclododecylamido)dimethyl(2-methyl-s-indacen-1-yl) silanetitanium(II) 1,4 diphenyl-1,3-butadiene,
(t-butylamido)dimethyl(3,4-(cyclopenta(I)phenanthren-1-yl)silanetitanium dimethyl,
(t-butylamido)dimethyl(3,4-(cyclopenta(I)phenanthren-1-yl)silanetitanium(II) 1,3-pentadiene,
(t-butylamido)dimethyl(3,4-(cyclopenta(I)phenanthren-1-yl)silanetitanium(II) 1,4 diphenyl-1,3-butadiene,
(cyclohexylamido)dimethyl(3,4-(cyclopenta(I) phenanthren-1-yl)silanetitanium dimethyl,
cyclohexylamido)dimethyl(3,4-(cyclopenta(I) phenanthren-1-yl)silanetitanium(II) 1,3-pentadiene,
cyclohexylamido)dimethyl(3,4-(cyclopenta(I) phenanthren-1-yl)silanetitanium(II) 1,4 diphenyl-1,3-butadiene,
(cyclododecylamido)dimethyl(3,4-(cyclopenta(I) phenanthren-1-yl)silanetitanium dimethyl,
(cyclododecylamido)dimethyl(3,4-(cyclopenta(I) phenanthren-1-yl)silanetitanium(II) 1,3-pentadiene,
(cyclododecylamido)dimethyl(3,4-(cyclopenta(I) phenanthren-1-yl)silanetitanium(II) 1,4 diphenyl-1,3-butadiene,
(t-butylamido)dimethyl(2-methyl-4-phenylinden-1-yl) silanetitanium dimethyl,
(t-butylamido)dimethyl(2-methyl-4-phenylinden-1-yl) silanetitanium(II) 1,3-pentadiene,
(t-butylamido)dimethyl(2-methyl-4-phenylinden-1-yl) silanetitanium(II) 1,4 diphenyl-1,3-butadiene,
(cyclohexylamido)dimethyl(2-methyl-4-phenylinden-1-yl)silanetitanium dimethyl,
cyclohexylamido)dimethyl(2-methyl-4-phenylinden-1-yl)silanetitanium(II) 1,3-pentadiene,
cyclohexylamido)dimethyl(2-methyl-4-phenylinden-1-yl)silanetitanium(II) 1,4 diphenyl-1,3-butadiene,
(cyclododecylamido)dimethyl(2-methyl-4-phenylinden-1-yl)silanetitanium dimethyl,
(cyclododecylamido)dimethyl(2-methyl-4-phenylinden-1-yl)silanetitanium(II) 1,3-pentadiene,
(cyclododecylamido)dimethyl(2-methyl-4-phenylinden-1-yl)silanetitanium(II) 1,4 diphenyl-1,3-butadiene,
(t-butylamido)dimethyl(2-methyl-4-phenylinden-1-yl) silanetitanium dimethyl,
(t-butylamido)dimethyl(2-methyl-4-phenylinden-1-yl) silanetitanium (II) 1,3-pentadiene,
(t-butylamido)dimethyl(2-methyl-4-phenylinden-1-yl) silanetitanium (II) 1,4 diphenyl-1,3-butadiene,
(cyclohexylamido)dimethyl(2-methyl-4-phenylinden-1-yl)silanetitanium dimethyl, cyclohexylamido)dimethyl(2-methyl-4-phenylinden-1-yl)silanetitanium(II) 1,3-pentadiene,
cyclohexylamido)dimethyl(2-methyl-4-phenylinden-1-yl)silanetitanium(II) 1,4 diphenyl-1,3-butadiene,
(cyclododecylamido)dimethyl(2-methyl-4-phenylinden-1-yl)silanetitanium dimethyl, (cyclododecylamido)dimethyl(2-methyl-4-phenylinden-1-yl)silanetitanium (II) 1,3-pentadiene,
(cyclododecylamido)dimethyl(2-methyl-4-phenylinden-1-yl)silanetitanium(II) 1,4 diphenyl-1,3-butadiene,
(t-butylamido)dimethyl(3-(1-pyrrolidinyl)inden-1-yl)silanetitanium dimethyl,
(t-butylamido)dimethyl(3-(1-pyrrolidinyl)inden-1-yl)silanetitanium(II) 1,3-pentadiene,
(t-butylamido)dimethyl(3-(1-pyrrolidinyl)inden-1-yl)silanetitanium(II) 1,4 diphenyl-1,3-butadiene,
(cyclohexylamido)dimethyl(3-(1-pyrrolidinyl)inden-1-yl)silanetitanium dimethyl,
cyclohexylamido)dimethyl(3-(1-pyrrolidinyl)inden-1-yl)silanetitanium(II) 1,3-pentadiene,
cyclohexylamido)dimethyl(3-(1-pyrrolidinyl)inden-1-yl)silanetitanium(II) 1,4diphenyl-1,3-butadiene,
(cyclododecylamido)dimethyl(3-(1-pyrrolidinyl)inden-1-yl)silanetitanium dimethyl,
(cyclododecylamido)dimethyl(3-(1-pyrrolidinyl)inden-1-yl)silanetitanium(II) 1,3-pentadiene,
(cyclododecylamido)dimethyl(3-(1-pyrrolidinyl)inden-1-yl)silanetitanium(II) 1,4 diphenyl-1,3-butadiene,
(t-butylamido)dimethyl(3-(1-pyrrolidinyl)inden-1-yl)silanetitanium dimethyl,
(t-butylamido)dimethyl(3-(1-pyrrolidinyl)inden-1-yl)silanetitanium (II) 1,3-pentadiene,
(t-butylamido)dimethyl(3-(1-pyrrolidinyl)inden-1-yl)silanetitanium (II) 1,4 diphenyl-1,3-butadiene,
(cyclohexylamido)dimethyl(3-(1-pyrrolidinyl)inden-1-yl)silanetitanium dimethyl,
cyclohexylamido)dimethyl(3-(1-pyrrolidinyl)inden-1-yl)silanetitanium(II) 1,3-pentadiene,
cyclohexylamido)dimethyl(3-(1-pyrrolidinyl)inden-1-yl)silanetitanium(II) 1,4 diphenyl-1,3-butadiene,
(cyclododecylamido)dimethyl(3-(1-pyrrolidinyl)inden-1-yl)silanetitanium dimethyl,
(cyclododecylamido)dimethyl(3-(1-pyrrolidinyl)inden-1-yl)silanetitanium(II) 1,3-pentadiene,
(cyclododecylamido)dimethyl(3-(1-pyrrolidinyl)inden-1-yl)silanetitanium(II) 1,4 diphenyl-1,3-butadiene,
1,2-ethanebis(inden-1-yl)zirconium dimethyl,
1,2-ethanebis(inden-1-yl)zirconium(II) 1,3-pentadiene,
1,2-ethanebis(inden-1-yl)zirconium(II) 1,4 diphenyl-1,3-butadiene,
1,2-ethanebis(2-methyl-4-phenylinden-1-yl)zirconium dimethyl,
1,2-ethanebis(2-methyl-4-phenylinden-1-yl)zirconium (II) 1,3-pentadiene,
1,2-ethanebis(2-methyl-4-phenylinden-1-yl)zirconium (II) 1,4 diphenyl-1,3-butadiene,
dimethylsilanebis(inden-1-yl)zirconium dimethyl,
dimethylsilanebis(inden-1-yl)zirconium(II) 1,3-pentadiene,
dimethylsilanebis(inden-1-yl)zirconium(II) 1,4 diphenyl-1,3-butadiene,
dimethylsilanebis(2-methyl-4-phenylinden-1-yl)zirconium dimethyl,
dimethylsilanebis(2-methyl-4-phenylinden-1-yl)zirconium(II) 1,3-pentadiene, and
dimethylsilanebis(2-methyl-4-phenylinden-1-yl)zirconium(II) 1,4 diphenyl-1,3-butadiene.

The expanded anion cocatalysts of the invention may also be used in combination with an oligomeric or polymeric alumoxane compound, a tri(hydrocarbyl)aluminum compound, a di(hydrocarbyl)(hydrocarbyloxy)aluminum compound, a di(hydrocarbyl)(dihydrocarbyl-amido) aluminum compound, a bis(dihydrocarbyl-amido) (hydrocarbyl)aluminum compound, a di(hydrocarbyl)amido (disilyl)aluminum compound, a di(hydrocarbyl)amido (hydrocarbyl)(silyl)aluminum compound, a bis (dihydrocarbylamido)(silyl)aluminum compound, or a mixture of the foregoing compounds, having from 1 to 20 non-hydrogen atoms in each hydrocarbyl, hydrocarbyloxy, or silyl group, if desired. These aluminum compounds are usefully employed for their beneficial ability to scavenge impurities such as oxygen, water, and aldehydes from the polymerization mixture.

Preferred aluminum compounds include $C_{1-20}$ trialkyl aluminum compounds, especially those wherein the alkyl groups are ethyl, propyl, isopropyl, n-butyl, isobutyl, pentyl, neopentyl, or isopentyl, dialkyl(aryloxy)aluminum compounds containing from 1–6 carbons in the alkyl group and from 6 to 18 carbons in the aryl group (especially (3,5-di (t-butyl)-4-methylphenoxy)diisobutylaluminum), methylalumoxane, modified methylalumoxane and diisobutylalumoxane. The molar ratio of metal complex to aluminum compound is preferably from 1:10,000 to 1000:1, more preferably from 1:5000 to 100:1, most preferably from 1:100 to 100:1.

The cocatalysts of the present invention are capable of activating a wide variety of metal complexes. Moreover, the cocatalysts can be optimized in their ability to activate different metal complexes through combination of anions, Z*, having Lewis base sites of varying base strength, and Lewis acids, J*, having varying acidity. Thus, use of weakly basic anions such as dicyanamide, 1,2,4-triazolide and 4,5-dichloroimidazolide give expanded anion salts which are less active cocatalysts, all other variables being the same, than moderately basic anions, such as cyanide, azide, benzotriazolide, benzimidazolide and tetraimidazoylborate, which in turn give less active cocatalalysts than even more basic anions, such as 4,4-dimethylimidazolinide, imidazolide, 5,6-dimethylbenzimidazolide and 2-undecylimidazolide. Moreover, more acidic Lewis acids, such as tris(pentafluorophenyl)alumane or tris (heptafluoronaphthyl)alumane give more active cocatalysts than do less acidic Lewis acid groups such as tris (pentafluorophenyl)borane or tris(heptafluoronaphthyl) borane. The highest activity cocatalysts have anions containing highly basic Lewis base sites in combination with highly acidic Lewis acids.

The equivalent ratio of catalyst/cocatalyst (calculated based on quantity of metal in the catalyst and anionic charges on the cocatalyst) employed preferably ranges from 1:10 to 10:1, more preferably from 1:5 to 2:1, most preferably from 1:4 to 1:1. Mixtures of the activating cocatalysts of the present invention may also be employed if desired.

Suitable addition polymerizable monomers include ethylenically unsaturated monomers, acetylenic compounds, conjugated or non-conjugated dienes, and polyenes. Preferred monomers include olefins, for examples alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, 1-pentene, 4-methylpentene-1,1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propene, 1-butene, 4-methyl-pentene-1,1-hexene, 1-octene, and combinations of ethylene and/or propene with one or more of such other alpha-olefins. Other preferred monomers include styrene, halo- or alkyl substituted styrenes, vinylbenzocyclobutene, 1,4-hexadiene, dicyclopentadiene, ethylidene norbornene, and 1,7-octadiene. Mixtures of the above-mentioned monomers may also be employed.

In general, the polymerization may be accomplished at conditions well known in the prior art for Ziegler-Natta or Kaminsky-Sinn type polymerization reactions. Suspension, solution, slurry, gas phase or high pressure, whether employed in batch or continuous form or other process conditions, may be employed if desired. Examples of such well known polymerization processes are depicted in WO 88/02009, U.S. Pat. Nos. 5,084,534, 5,405,922, 4,588,790, 5,032,652, 4,543,399, 4,564,647, 4,522,987, and elsewhere. Preferred polymerization temperatures are from 0–250° C. Preferred polymerization pressures are from atmospheric to 3000 atmospheres.

Preferred processing conditions include solution polymerization, more preferably continuous solution polymerization processes, conducted in the presence of an aliphatic or alicyclic liquid diluent. By the term "continuous polymerization" is meant that at least the products of the polymerization are continuously removed from the reaction mixture, such as for example by devolatilization of a portion of the reaction mixture. Preferably one or more reactants are also continuously added to the polymerization mixture during the polymerization. Examples of suitable aliphatic or alicyclic liquid diluents include straight and branched-chain $C_{4-12}$ hydrocarbons and mixtures thereof; alicyclic hydrocarbons such as cyclohexane, cycloheptane, methylcyclohexane, methylcycloheptane, and mixtures thereof; and perfluorinated hydrocarbons such as perfluorinated $C_{4-10}$ alkanes, and the like. Suitable diluents also include aromatic hydrocarbons (particularly for use with aromatic a-olefins such as styrene or ring alkyl-substituted styrenes) including toluene, ethylbenzene or xylene, as well as liquid olefins (which may act as monomers or comonomers) including ethylene, propylene, butadiene, cyclopentene, 1-hexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable. The foregoing diluents may also be advantageously employed during the synthesis of the metal complexes and catalyst activators of the present invention.

In most polymerization reactions the molar ratio of catalyst:polymerizable compounds employed is from $10^{-12}$:1 to $10^{-1}$:1, more preferably from $10^{-12}$:1 to $10^{-5}$:1.

The catalyst composition of the invention may also be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770 now abandoned. A more specific process is disclosed in copending application U.S. Ser. No. 08/10958, filed Jan. 29, 1993 now abandoned. The teachings of the foregoing publications and pending applications are hereby incorporated by reference.

Molecular weight control agents can be used in combination with the present cocatalysts. Examples of such molecular weight control agents include hydrogen, trialkyl aluminum compounds or other known chain transfer agents. A particular benefit of the use of the present cocatalysts is the ability (depending on reaction conditions) to produce narrow molecular weight distribution a-olefin homopolymers and copolymers in greatly improved catalyst efficiencies. Preferred polymers have Mw/Mn of less than 2.5, more preferably less than 2.3. Such narrow molecular weight distribution polymer products are highly desirable due to improved tensile strength properties.

The catalyst composition of the present invention can also be employed to advantage in the gas phase polymerization and copolymerization of olefins. Gas phase processes for the polymerization of olefins, especially the homopolymerization and copolymerization of ethylene and propylene, and the copolymerization of ethylene with higher alpha olefins such as, for example, 1-butene, 1-hexene, 4-methyl-1-pentene are well known in the art. Such processes are used commercially on a large scale for the manufacture of high density polyethylene (HDPE), medium density polyethylene (MDPE), linear low density polyethylene (LLDPE) and polypropylene.

The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate, the fluidisation grid, by a flow of fluidisation gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and one or more heat exchangers to strip the gas of the heat of polymerization.

A preferred method of cooling of the bed, in addition to the cooling provided by the cooled recycle gas, is to feed a volatile liquid to the bed to provide an evaporative cooling effect. The volatile liquid employed in this case can be, for example, a volatile inert liquid, for example, a saturated hydrocarbon having about 3 to about 8, preferably 4 to 6, carbon atoms. In the case that the monomer or comonomer itself is a volatile liquid, or can be condensed to provide such a liquid this can be suitably be fed to the bed to provide an evaporative cooling effect. Examples of olefin monomers which can be employed in this manner are olefins containing from about 3 to about eight, preferably from 3 to six carbon atoms. The volatile liquid evaporates in the hot fluidized bed to form gas which mixes with the fluidizing gas. If the volatile liquid is a monomer or comonomer, it will undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream, as described, for example, in EP-A-89691, U.S. Pat. No. 4,543,399, WO 94/25495 and U.S. Pat. No. 5,352,749, which are hereby incorporated by reference. A particularly preferred method of recycling the liquid to the bed is to separate the liquid from the recycle gas stream and to reinject this liquid directly into the bed, preferably using a method which generates fine droplets of the liquid within the bed. This type of process is described in WO 94/28032, the teachings of which are also hereby incorporated by reference.

The polymerization reaction occurring in the gas fluidized bed is catalyzed by the continuous or semi-continuous addition of catalyst. Such catalyst can be supported on an inorganic or organic support material if desired. The catalyst can also be subjected to a prepolymerization step, for example, by polymerizing a small quantity of olefin monomer in a liquid inert diluent, to provide a catalyst composite comprising catalyst particles embedded in olefin polymer particles.

The polymer is produced directly in the fluidized bed by catalyzed (co)polymerization of the monomer(s) on the fluidized particles of catalyst, supported catalyst or prepolymer within the bed. Start-up of the polymerization reaction is achieved using a bed of preformed polymer particles, which, preferably, is similar to the target polyolefin, and conditioning the bed by drying with inert gas or nitrogen prior to introducing the catalyst, the monomer(s) and any other gases which it is desired to have in the recycle gas stream, such as a diluent gas, hydrogen chain transfer agent, or an inert condensable gas when operating in gas phase condensing mode. The produced polymer is discharged continuously or discontinuously from the fluidized bed as desired, optionally exposed to a catalyst kill and optionally pelletized.

EXAMPLES

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. The term "overnight", if used, refers to a time of approximately 16–18 hours, "room temperature", if used, refers to a temperature of about 20–25° C., and "mixed alkanes" refers to a mixture of mostly $C_6$-$C_{12}$ alkanes available commercially under the trademark Isopar E™ from Exxon Chemicals Inc.

All manipulation of air sensitive materials was performed in an argon filled, vacuum atmospheres, glove box or on a high vacuum line using standard Shlenk techniques. Toluene was purified by passage through columns packed with activated alumina (Kaiser A-2) and supported copper (Engelhard, Cu-0224 S). Hexanes were purified by distillation from sodium benzophenone ketyl. Tris (pentafluorophenyl)borane (TPB) was purchased from Boulder Scientific. Potassium benzyl was prepared from Schlosser's base generated in toluene. n-Butylferrocene was purchased from Alfa and used without further purification. Imidazole, dichloromethane (anhydrous, sure-seal), 18-crown-6, chlorotriphenylmethane, iodine and salts not mentioned above were purchased from Aldrich and used as received. Potassium azide was purchased from Atomergic Chemetals Corp., and used as received. Dioctadecylmethylamine was purchased from Akzo-Nobel (Armeen M2HT), and used as received.

Example 1

Potassium bis(tris(Pentafluorophenyl)borane)azide ($K((C_6F_5)_3B)_2N_3$)

Potassium azide (238.0 mg, 2.930 mmol), TPB (3000.0 mg, 5.859 mmol), 18-crown-6 (7.7 mg, 0.029 mmol) and toluene (21 mL) were placed in a 50 mL flask and heated to reflux under argon. After 16 hours the mixture was cooled, a fine colorless solid allowed to settle and the supernatant decanted. The solid was washed with three 7 mL portions of toluene and dried in vacuo. Yield, 3075 mg, 94.97 percent.
Dioctadecylmethylammonium bis(tris(Pentafluorophenyl)borane)azide ($[(C_{18}H_{37})_2CH_3NH][((C_6F_5)_3B)_2N_3]$)

Potassium bis(tris(pentafluorophenyl)borane)azide (1500.0 mg, 1.3573 mmol) and dioctadecylmethylammonium chloride (777.0 mg, 1.3573 mmol) were placed in a 50 mL flask. The solids were cooled to −78° C. and taken up in 20 mL of dichloromethane, added via syringe under argon counter-flow. As the stirred mixture warmed, the original solids dissolved and a fine precipitate of a colorless solid formed. The solid was removed by filtration and washed with two 5 mL portions of dichloromethane. The filtrate stripped under high vacuum, giving a colorless oil. Yield, 1646 mg, 75.33 percent.

Example 2

Sodium bis(tris(Pentafluorophenyl)borane)dicyanamide ($K((C_6F_5)_3B)_2NCNCN$)

Sodium dicyanamide (173.9 mg, 1.953 mmol), TPB (2000.0 mg, 3.9063 mmol), 18-crown-6 (5.2 mg, 0.0020 mmol) and toluene (21 mL) were placed in a 50 mL flask and heated to reflux under argon. After 4 hours the mixture was cooled, a colorless liquid allowed to settle and the upper layer discarded. The dense, mobile liquid was washed with three 7 mL portions of toluene and dried in vacuo to a colorless glassy solid. Yield, 1658.9 mg, 76.32 percent.
Dioctadecylmethylammonium bis(tris(Pentafluorophenyl) borane)dicyanamide ($[(C_{18}H_{37})_2CH_3N H][((C_6F_5)_3B)_2 NCNCN]$)

Sodium bis(tris(pentafluorophenyl)borane)dicyanamide (1000.0 mg, 0.8985 mmol) and dioctadecylmethylammonium chloride (514.4 mg, 0.8985 mmol) were placed in a 50 mL flask . The solids were taken up in 20 mL of dichloromethane, added via syringe under argon counter-flow. As the mixture stirred, the original solids dissolved and a fine precipitate of a colorless solid formed. The solid was removed by filtration and washed with two 5 mL portions of dichloromethane. The filtrate was stripped under high vacuum, giving a pale beige, viscous, oil. Yield, 747.5 mg, 51.13 percent.

Example 3

Potassium Imidazolide ($KC_3H_3N_2$)

Imidazole (261.4 mg, 3.840 mmol), potassium benzyl (500.0 mg, 3.839 mmol) and toluene (14 mL) were combined in a 25 mL flask and heated to reflux under argon. The red-orange potassium benzyl color faded as the mixture reached reflux, leaving a slurry of colorless solid. After 4 hours the mixture was cooled, the solid isolated by filtration and dried in vacuo, giving 383.8 mg of white powder, 94.16 percent yield.

Potassium bis(tris(Pentafluorophenyl)borane)imidazolide $(K((C_6F_5)_3B)_2C_3H_3N_2)$ Potassium imidazolide (311.1 mg, 2.930 mmol), TPB (3000.0 mg, 5.8594 mmol), 18-crown-6 (7.7 mg, 0.0029 mmol) and toluene (21 mL) were placed in a 50 mL flask and heated to reflux under argon. After 16 hours the mixture was cooled, a colorless solid allowed to settle and the upper layer discarded. The solid was washed with three 14 mL portions of toluene and dried in vacuo to a bone-white solid. Yield, 3402 mg, 102.7 percent.

Dioctadecylmethylammonium bis(tris(Pentafluorophenyl)borane)imidazolide $([(C_{18}H_{37})_2CH_3NH][((C_6F_5)_3B)_2C_3H_3N_2])$ Potassium bis(tris(pentafluorophenyl)borane)imidazolide (1000.0 mg, 0.8181 mmol) and dioctadecylmethylammonium chloride (468.3 mg, 0.8180 mmol) were placed in a 50 mL flask on a flip-frit. The solids were taken up in 20 mL of dichloromethane, added via syringe under argon counter-flow. As the mixture stirred, the original solids dissolved and a fine precipitate of a colorless solid formed. The solid was removed by filtration and washed with two 10 mL portions of dichloromethane. The filtrate was stripped under high vacuum, giving a pale yellow, viscous, oil. Yield, 1259.1 mg, 94.52 percent.

2) Imidazole (0.1330 g, 1.954 mmol), tris(pentafluorophenyl)borane (2.0000 g, 3.9063 mmol) and dioctadecylmethylamine (1.0469 g, 1.9531 mmol) were placed in a 50 mL flask, taken up in 21 mL of toluene and refluxed under argon for 16 hours. The volatiles were then stripped under vacuum, giving 2.8591 g of viscous, tan oil, 89.91 percent yield.

Example 4

Sodium Tetrakis(tris(pentafluorophenyl)borane)tetraimidazoylborate $(Na((C_6F_5)_3BC_3H_3N_2)_4B))$ Sodium tetraimidazoylborate (295.0 mg, 0.9766 mmol), TPB (2000.0 mg, 3.9063 mmol), 18-crown-6 (2.6 mg, 0.010 mmol) and toluene (21 mL) were placed in a 50 mL flask and heated to reflux under argon. After 16 hours the mixture was cooled, a beige oil allowed to settle and the upper layer discarded. The oil was washed with one 14 mL portion of toluene and dried in vacuo to an off white solid. Yield, 2236.7 mg, 97.46, percent.

Dioctadecylmethylammonium Tetrakis(tris(pentafluorophenyl)borane)tetraimidazoylborate $([(C_{18}H_{37})_2 CH_3NH][((C_6F_5)_3BC_3H_3N_2)_4B)])$ Sodium tetrakis(trispentafluorophenyl)tetraimidazoylborate (1500.0 mg, 0.6383 mmol) and dioctadecylmethylammonium chloride (365.4 mg, 0.6383 mmol) were placed in a 50 mL flask on a flip-frit. The solids were taken up in 20 mL of dichloromethane, added via syringe under argon counter-flow. As the mixture stirred, the original solids dissolved and a fine precipitate of a colorless solid formed. The solid was removed by filtration and washed with two 10 mL portions of dichloromethane. The filtrate was stripped under high vacuum, giving a beige glass. Yield, 1685.0 mg, 92.17 percent.

Example 5

Dioctadecylmethylammonium bis(tris(Pentafluorophenyl)borane)benzotriazolide $([(C_{18}H_{37})_2CH_3NH][((C_6F_5)_3B)_2C_3H_3N_2])$ Benzotriazole (0.2327 g, 1.953 mmol), tris(pentafluorophenyl)borane (2.0000 g, 3.9063 mmol) and dioctadecylmethylamine (1.0469 g, 1.9531 mmol) were placed in a 50 mL flask, taken up in 21 mL of toluene and refluxed under argon for 4 hours. The volatiles were then stripped under vacuum, giving 2.3 g of very sticky beige glass (70 percent).

Example 6

Dioctadecylmethylammonium bis(tris(Pentafluorophenyl)borane)-5,6-dimethylbenzimidazolide $([(C_{18}H_{37})_2CH_3NH][((C_6F_5)_3B)_2C_9H_9N_2])$ 5,6-dimethylbenzimidazole (0.2855 g, 1.953 mmol), tris(pentafluorophenyl)borane (2.0000 g, 3.9063 mmol) and dioctadecylmethylamine (1.0469 g, 1.9531 mmol) were placed in a 50 mL flask, taken up in 21 mL of toluene and refluxed under argon for 16 hours. The volatiles were then stripped under vacuum. Yield, 3.060 g, 91.84 percent.

Example 7

Dioctadecylmethylammonium bis(tris(Pentafluorophenyl)borane)benzimidazolide $([(C_{18}H_{37})_2CH_3NH][((C_6F_5)_3B)_2C_7H_5N_2])$ Benzimidazole (0.2307 g, 1.953 mmol), tris(pentafluorophenyl)borane (2.0000 g, 3.9063 mmol) and dioctadecylmethylamine (1.0469 g, 1.9531 mmol) were placed in a 50 mL flask, taken up in 21 mL of toluene and refluxed under argon for 3.5 hours. The volatiles were then stripped under vacuum. Yield, 2.993 g, 91.33 percent.

Example 8

Dioctadecylmethylammonium bis(tris(Pentafluorophenyl)borane)-4,5-dichloroimidazolide $([(C_{18}H_{37})_2CH_3NH][((C_6F_5)_3B)_2C_7H_5N_2])$ 4,5-dichloroimidazole (0.2675 g, 1.953 mmol), tris(pentafluorophenyl)borane (2.0000 g, 3.9063 mmol) and dioctadecylmethylamine (1.0469 g, 1.9531 mmol) were placed in a 50 mL flask, taken up in 21 mL of toluene and refluxed under argon for hours. The volatiles were then stripped under vacuum. Yield, 2.937 g, 88.62 percent.

Example 9

Dioctadecylmethylammonium bis(tris(Pentafluorophenyl)borane)-4,5-diphenylimidazolide $([(C_{18}H_{37})_2CH_3NH][((C6F_5)_3B)_2C_7H_5N_2])$ 4,5-diphenylimidazole (0.4302 g, 1.953 mmol), tris(pentafluorophenyl)borane (2.0000 g, 3.9063 mmol) and dioctadecylmethylamine (1.0469 g, 1.9531 mmol) were placed in a 50 mL flask, taken up in 21 mL of toluene and refluxed under argon for 15 hours. The volatiles were then stripped under vacuum. Yield, 3.217 g, 92.52 percent.

Example 10

Dioctadecylmethylammonium bis(tris(Pentafluorophenyl)borane)-1,2,4-triazolide $([(C_{18}H_{37})_2CH_3NH][((C_6F_5)_3B)_2C_7H_5N_2])$ 1,2,4-triazole (0.1349 g, 1.953 mmol), tris(pentafluorophenyl)borane (2.0000 g, 3.9063 mmol) and dioctadecylmethylamine (1.0469 g, 1.9531 mmol) were placed in a 50 mL flask, taken up in 21 mL of toluene and refluxed under argon for 5 hours. The volatiles were then stripped under vacuum. Yield, 2.702 g, 84.92 percent.

Example 11

Potassium bis(tris(Pentafluorophenyl)borane)cyanide $(K((C6F_5)_3B)_2CN)$

Potassium cyanide (65.1 mg, 1.000 mmol), TPB (1024 mg, 2.000 mmol), 18-crown-6 (2.6mg, 0.010 mmol) and toluene (20 mL) were placed in a 50 mL flask, stirred and heated to reflux under argon. After 24 hours the mixture was cooled, a fine colorless solid allowed to settle and the supernatant decanted. The solid was washed with two 3.5 mL portions of toluene and dried in vacuo. Yield, 854.9 mg, 78.5 percent.

Triphenylcarbenium bis(tris(Pentafluorophenyl)borane) cyanide ([Ph$_3$C][((C$_6$F$_5$)$_3$B)$_2$CN])

Potassium bis(tris(pentafluorophenyl)borane)cyanide (827.5 mg, 0.7598 mmol) and chlorotriphenylmethane (211.8 mg, 0.7597 mmol) were placed in a 50 mL flask. The stirred solids were taken up in 10 mL of dichloromethane, added via syringe under argon counter-flow. An immediate reaction gave a deep yellow solution and a colorless solid. The solid was removed by filtration and washed (four times 4 mL) until all color was gone. The filtrate was reduced under vacuum to 4 mL, cooled to −78° C. and diluted with 10 mL of hexanes. The resulting suspension of brown oil was allowed to warm and stir. The oil solidified and then digested to a canary-yellow solid after stirring for 30 minutes. The yellow solid was isolated by filtration and dried under high vacuum. Yield, 935.3 mg, 95.20 percent.

Example 12

Potassium bis(tris(Pentafluorophenyl)borane)cyanide-$^{13}$C (K((C$_6$F$_5$)$_3$B)$_2$$^{13}$CN)

Potassium cyanide-$^{13}$C (193.7 mg, 2.930 mmol), TPB (3000.0 mg, 5.859 mmol), 18-crown-6 (7.7 mg, 0.029 mmol) and toluene (25 mL) were placed in a 50 mL flask, stirred and heated to reflux under argon. After 24 hours the mixture was cooled, a fine colorless solid allowed to settle and the supernatant decanted. The solid was washed with three 14 mL portions of toluene and dried in vacuo. Yield, 3020 mg, 94.7 percent.

Dioctadecylmethylammonium bis(tris(Pentafluorophenyl) borane)cyanide-$^{13}$C ([(C$_{18}$H$_{37}$)$_2$CH$_3$NH][((C$_6$F$_5$)$_3$B)$_2$$^{13}$CN])

Potassium bis(tris(pentafluorophenyl)borane)cyanide-$^{13}$C (1500.0 mg, 1.3760 mmol) and dioctadecylmethylammonium chloride (787.7 mg, 1.3760 mmol) were placed in a 50 mL flask. The solids were cooled to −78° C. and taken up in 20 mL of dichloromethane, added via syringe under argon counter-flow. As the stirred mixture warmed, the original solids dissolved and a fine precipitate of a colorless solid formed. The solid was removed by filtration and washed with 10 mL of dichloromethane. The filtrate stripped under high vacuum, giving an almost colorless, extremely viscous, oil. Yield, 1646 mg, 75.33 percent.

Example 13 n-Butylferocenium Triiodide ([(C$_5$H$_5$)((C$_4$H$_9$)C$_5$H$_4$)Fe)][I$_3$])

n-Butylferrocene (5.0 g, 21 mmol), iodine (8.1 g, 32 mmol) and 50 mL of absolute ethanol were placed in a flask. The mixture was stirred and heated to 45 C with a warm water bath and kept warm for one hour. The resulting dark crystalline solid was isolated by filtration, washed with four 25 mL portions of ethanol and air dried. Yield, 12.2 g, 93 percent.

n-Butylferrocenium bis(tris(Pentafluorophenyl)borane) cyanide-$^{13}$C ([(C$_5$H$_5$)((C$_4$H$_9$)C$_5$H$_4$)Fe][((C$_6$F$_5$)$_3$B)$_2$$^{13}$CN])

Potassium bis(tris(pentafluorophenyl)borane)cyanide-$^{13}$C (875.1 mg, 0.8028 mmol) and n-butylferrocenium triiodide (500.0 mg, 0.8028 mmol) were placed in a 50 mL flask. The stirred solids were taken up in 20 mL of dichloromethane, added via syringe under argon counter-flow. The mixture was stirred for an additional 15 minutes and then filtered to remove a colorless solid, which was washed with two 5 mL portions of solvent. The clear yellow-violet filtrate was reduced to 5 mL in vacuo, cooled to −78° C. and the resulting blue crystals isolated by filtration and dried in vacuo. Yield, 690.7 mg, 66.5 percent.

Example 14

Dioctadecylmethylammonium 1,3-bis(tris (Pentafluorophenyl)borane)-4,4-dimethylimidazolinide ([(C$_{18}$H$_{37}$)$_2$CH$_3$NH][((C$_6$F$_5$)$_3$B)$_2$C$_5$H$_9$N$_2$])

4,4-dimethylimidazoline (0.192 g, 1.95 mmol) was added dropwise to a mixture of tris(pentafluorophenyl)borane (2.00 g, 3.91 mmol), dioctadecylmethylamine (1.05 g, 1.95 mmol) and 21 mL of toluene in a 50 mL flask, stirred and refluxed under argon for 5 hours. The volatiles were then stripped under vacuum, giving 2.54 g of sticky yellow glass. Yield was 78.3 percent.

Example 15

Dioctadecylmethylammonium 1,3-bis(tris (Pentafluorophenyl)alumane)imidazolide ([(C$_{18}$H$_{37}$)$_2$CH$_3$NH][((C$_6$F$_5$)$_3$Al)$_2$C$_3$H$_3$N$_2$])

Imidazole (0.064 g, 0.947 mmol), tris(pentafluorophenyl) alumane (1.000 g, 1.89 mmol) and dioctadecylmethylamine (0.507 g, 0.947 mmol) were placed in a 50 mL flask, taken up in 21 mL of toluene and refluxed under argon for 5 hours. The volatiles were then stripped under vacuum, giving 1.46 g of viscous beige oil (92.6 percent yield).

Example 16

Dioctadecylmethylammonium 1,3-bis(tris (Pentafluorophenyl)alumane)-2-undecylimidazolide ([(C$_{18}$H$_{37}$)$_2$CH$_3$NH][((C$_6$F$_5$)$_3$Al)$_2$C$_3$H$_3$N$_2$])

Undecylmidazole (0.267 g, 1.20 mmol), tris (pentafluorophenyl)alumane (1.27 g, 2.40 mmol) and dioctadecylmethylamine (0.64 g, 1.20 mmol) were placed in a 50 mL flask, taken up in 10 mL of lsopar-E and refluxed under argon for 4.5 hours. The volatiles were then stripped under vacuum, giving 2.18 g of viscous beige oil (100 percent yield).

Metal Complex Preparations

In the following polymerizations certain of the metal complexes used were prepared in the following manner.

Anhydrous C$_6$D$_6$ and CH$_2$Cl$_2$ were purchased from Aldrich and used as received.

NMR spectra were recorded on a Varian XL-300 instrument ($^1$H, 300 MHz; $^{13}$C{$^1$H}, 75 MHz). MeLi, bis (dichloromethylsilyl)ethane, triethylamine and tert-butylamine were purchased from Aldrich and used as received. Bis(dichloromethylsilyl)hexane (United Chemical Technologies), n-butyllithium (ACROS) and 2-methyl-4-phenylindene (Boulder Scientific) were used as received. 1-N-pyrrolidineindene was prepared via the route of Noland, et al., JOC, 1981, 46, (1940) It's lithium salt, (1-(1-pyrrolidinyl)-1H-indenyl)lithium, was prepared by reaction with butyllithium in hexanes and recovered by filtration. $^1$H and $^{13}$C{$^1$H} NMR spectra are reported relative to tetramethylsilane and are referenced to the residual solvent peak.

Preparation 1

(μ-((1,1'-(1,6-Hexanediyl)bis(N-(1,1-dimethylethyl)-1-methyl-1-((1,2,3,3a,7a-n)-3-(1-pyrrolidinyl)-1H-inden-1-yl) silanaminato-KN)(4-))))tetrachloroditianium

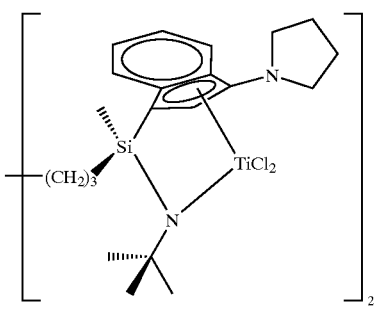

A) 1,1'-(1,6-Hexanediyl)bis(1-chloro-N-(1,1-dimethylethyl)-1-methyl)-silanamine

To a −10° C. solution of 1,6-bis(chloromethylsilyl)hexane (25.00 g, 80.1 mmol) and triethylamine (24.6 mL, 0.176 mole) in 250 mL of dichloromethane was added dropwise over 1 hour a solution of tert-butylamine (16.8 mL, 0.160 mole) in 100 mL of dichloromethane. The suspension was allowed to warm to room temperature. After stirring overnight, most to the volatiles were removed in vacuo. The product was extracted into 175 mL of hexanes, filtered and the hexanes removed in vacuo to leave 29.5 g (96 percent yield) of 1,1'-(1,6-hexanediyl)bis(1-chloro-N-(1,1-dimethylethyl)-1-methyl)silanamine as a pale-pink viscous liquid.

$^1$H NMR ($C_6D_6$): 1.35 (m, 4H), 1.24 (m, 4H), 1.13 (s, 18H), 1.03 (br s, 2H), 0.75 (m, 4H), 0.33 (s, 6H). $^{13}C\{^1H\}$ ($C_6D_6$): 50.35, 33.42, 32.95, 23.74, 20.34, 3.12.

B) 1,1'-(1,6-Hexanediyl)bis(N-(1,1-dimethylethy)-1-methyl-1-(3-(1-pyrrolidinyl)-1H-inden-1-yl)-silanamine To a −30° C. solution of 1,6-bis(N-(tert-butyl)-1-chloro-1-methylsilanamine)hexane (1.50 g, 3.89 mmol) in 20 mL of THF was added a precooled (−30° C.) solution of (1-(1-pyrrolidinyl)-1H-indenyl)lithium (1.49 g, 7.78 mmol) in 10 mL of THF. The reaction was allowed to warm to room temperature as it gradually darkened and changed to a deep-red/purple solution with slight green flourescence. After 16 hours, the volatiles were removed in vacuo and 50 mL of hexanes added. The suspension was filtered and hexanes removed from the filtrate in vacuo to leave 2.5 g (92 percent yield) of 1,1'-(1,6-hexanediyl)bis(N-(1,1-dimethylethyl)-1-methyl-1-(3-(1-pyrrolidinyl)-1H-inden-1-yl)-silanamine as a red/purple oil.

$^1$H NMR ($C_6D_6$): 7.71 (m, 4H), 7.27 (m, 4H), 5.47/5.43 (2s, 2H, isomers), 3.51 (s, 2H), 3.29 (br s, 8H), 1.64 (sh m, 8H), 1.30 (m, 8H), 1.11 (set of several sharp peaks, 18H), 0.616 (br s, 2H), 0.50 (s, 4H), 0.20/0.04 (2 singlets, 6H, isomers). $^{13}C\{^1H\}$ ($C_6D_6$): 149.21, 146.99, 141.66, 124.85, 124.63, 123.95, 123.82, 120.95, 105.11, 50.86, 49.54, 43.20 (m), 34.05, 25.42, 24.51, 17.25/16.19 (isomers), −0.71/−1.88 (isomers).

C) 1,1'-(1,6-Hexanediyl)bis(N-(1,1-dimethylethyl)-1-methyl-1-(3-(1-pyrrolidinyl)-1H-inden-1-yl)-2, (deloc-1,2,3,3a,7a:1',2',3',3'a,7'a)-silanamine, Dilithium, Dilithium Salt To a solution of 1,6-bis((N-(tert-butyl)-1-methyl-1-(3-(1-pyrrolidinyl)-1H-inden-1-yl)silanamine))hexane (2.45 g, 3.6 mmole) in 50 mL of toluene was added over 15 minutes a solution of n-butyl lithium in hexanes (1.60 M, 9.42 mL, 15.0 mmol). Over the period of addition, the original red solution turns orange followed by formation of a yellow precipitate. After stirring for 14 hours, the yellow precipitate was collected by filtration and washed twice with 10 mL of toluene and then twice with 10 mL of hexanes. The dark yellow solid was dried in vacuo for 8 hours to leave 2.6 g (quantitive yield) of the desired product.

D) (μ-((1,1'-(1,6-Hexanediyl)bis(N-(1,1-dimethylethyl)-1-methyl-1-((1,2,3,3a,7a-η)-3-(1-pyrrolidinyl)-1H-inden-1-yl)silanaminato-κN)(4-))))tetrachlorodititanium To a precooled (−30° C.) suspension of $TiCl_3(THF)_3$ (1.42 g, 3.82 mmol) in 30 mL of THF was added a precooled (−30° C.) 30 mL THF solution of 1,6-bis((N-(tert-butyl)-1-methyl-1-(3-(1-pyrrolidinyl)-1H-inden-1-yl)silanamine)) hexane, tetralithium salt (1.35 g, 1.91 mmol). Immediately the color changed to very dark blue/green. After stirring at room temperature for 45 minutes, $PbCl_2$ (0.8 g, 2.879 mmol) was added. The color gradually changed to dark blue/purple as lead balls formed. After 1 hour, the volatiles were removed in vacuo and the product extracted into 25 mL of toluene, filtered and the volatiles removed in vacuo. The dark blue/purple residue was dried in vacuo for 4 hours and then triturated in hexanes (30 mL). The hexanes were removed in vacuo and 30 mL of hexanes was added followed by trituration again. The resulting purple/black suspension was filtered, the solid washed with hexanes and dried in vacuo overnight to leave 1.42 g (83 percent yield) of the desired product as a purple/black solid.

$^1$H NMR ($C_6D_6$): 7.62 (br s, 4H), 7.08 (br s, 4H), 5.67 (m, 2H), 3.58 (br s, 4H), 3.22 (br s, 4H), 1.49 (br s, 36 H), 1.8–0.50 (m, 23H). $^{13}C\{^1H\}$ ($C_6D_6$): 149.7 (m), 136.5, 135.5, 129.04, 128.9, 127.2, 126.4, 125.3, 106.77/106.29 (isomers), 92.3, 60.9, 50.6, 25.7, 24.3/24.0 (isomers), 19.7, 18.19, 14.34, 1.87/−0.54 (isomers).

Preparation 2

(μ-((1,1'-(1,6-Hexanediyl)bis(N-(1,1-dimethylethyl)-1-methyl-1-((1,2,3,3a,7a-η)-3-(1-pyrrolidinyl)-1H-inden-1-yl)silanaminato-κN)(4-))))tetramethyldititanium

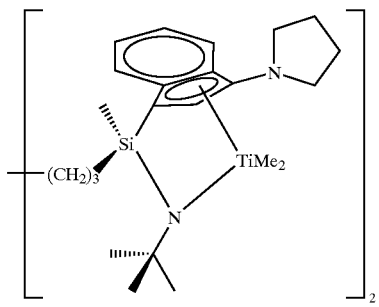

To a suspension of (μ-((1,1'-(1,6-hexanediyl)bis(N-(1,1-dimethylethyl)-1-methyl-1-((1,2,3,3a,7a-η)-3-(1-pyrrolidinyl)-1H-inden-1-yl)silanaminato-κN)(4-)))) tetrachlorodititanium (0.189 g, 0.21 mmol) in 10 mL of diethyl ether was added a solution of MeLi (1.4 M/$Et_2O$, 0.59 mL, 0.82 mmol). Instantly the solution turned dark red. After stirring at room temperature for 1 hour, the volatiles were removed in vacuo and the product extracted into 20 mL of hexanes. The suspension was filtered and the brown filter cake washed until no appreciable red color appeared in the washing. The volatiles were removed from the red filtrate and the residue dried in vacuo for 1 hour. The residue was extracted into hexanes (15 mL) and filtered to remove trace amounts of fine particulates. The hexanes were removed from the filtrate in vacuo and the resulting red 'flaky' solid dried in vacuo overnight to leave 0.130 g (75 percent yield) of red solid.

$^1$H NMR ($C_6D_6$): 7.73 (m, 2H), 7.50 (m, 2H), 7.04 (m, 2H), 6.89 (m, 2H), 5.42 (m, 2H), 3.43 (m, 4H), 3.25 (m, 4H), 1.53 (sh m, 36H), 1.8–0.50 (m, 20 H), 0.09 (br s, 6H), $^{13}C\{^1H\}$ (C6D6): 144.16 (m), 133.99, 133.31, 125.60, 125.13, 124.73, 123.90, 104.642, 104.02, 83.90, 57.78, 54.34, 54.13, 50.63, 48.86, 34.91, 33.99, 33.86, 26.05, 24.73, 24.38, 20.84, 19.20, 2.86, 0.39.

Preparation 3
($\mu$-((1,1'-(1,2-Ethanediyl)bis(N-(1,1-dimethylethyl)-1-methyl-1-((1,2,3,3a7a-$\eta$)-3-(1-pyrrolidinyl)-1H-inden-1-yl) silanaminato-$\kappa$N)(4-))))tetrachlorodititanium

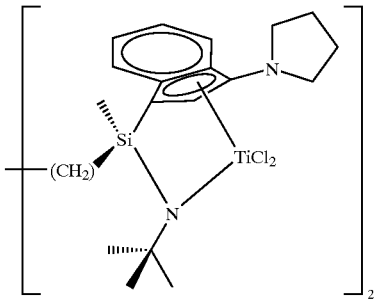

A) 1,1'-(1,2-Ethanediyl)bis(1-chloro-N-(1,1-dimethylethyl)-1-methyl)silanamine

To a $-10°$ C. solution of and 1,6-bis(dichloromethylsilyl) ethane (5.00 g, 19.5 mmol) and triethylamine (6.0 mL, 43 mmol) in 50 mL of $CH_2Cl_2$ was added dropwise over 1 hour a solution of tert-butylamine (4.1 mL, 39.0 mmol) in 20 mL of $CH_2Cl_2$. The obtained white suspension was allowed to warm to room temperature. After stirring for 16 hours, most of the solvent was removed in vacuo and 75 mL of hexanes added. The resulting suspension was filtered and the volatiles removed from the filtrate in vacuo to leave 1,6-bis(N-(tert-butyl)-1-chloro-1-methylsilanamine)ethane (5.7 g, 97 percent yield) as a pale pink oily solid.

$^1$H NMR ($C_6D_6$): 1.12 (s, 18H), 1.03 (br s, 2H), 0.91 (m, 4H), 0.33/0.32. (two s, 6H, isomers). $^{13}C\{^1H\}$ ($C_6D_6$): 50.36, 33.32, 32.95, 12.65/12. (two peaks/isomers), 2.39/2.13 (two peaks/isomers).

B) 1,1'-(1,2-Ethanediyl)bis(N-(1,1-dimethylethyl)-1-methyl-1-(3-(1-pyrrolidinyl)-1H-inden-1-yl)-silanamine To a $-30°$ C. solution of (1-(1-pyrrolidinyl)-1H-indenyl) lithium (1.705 g, 8.92 mmol) in 10 mL of THF was added a $-30°$ C. solution of 1,6-bis(N-(tert-butyl)-1-chloro-1-methylsilanamine)ethane (1.47 g, 4.46 mmol) in 5 mL of THF. The reaction was allowed to warm to room temperature as it gradually darkened and changed to a deep-red/purple solution with slight green fluorescence. After 16 hrs at room temperature, the volatiles were removed in vacuo and then 50 mL of hexanes was added. The suspension was filtered and the hexanes removed from the filtrate in vacuo to leave 1,6-bis((N-(tert-butyl)-1-methyl-1-(3-(1-pyrrolidinyl)-1H-inden-1-yl)silanamine)ethane (2.7 g, 97 percent yield) as a red/purple oil.

$^1$H NMR ($C_6D_6$): 7.75–7.55 (m, 4H), 7.40–7.15 (m, 4H), 5.42 (m, 2H), 3.505 (m, 2H), 3.29 (br s, 8H), 1.65 (br s, 8H), 1.09 (set of several sharp peaks, 18H), 0.88 (m, 2H), 0.54 (m, 4H), 0.45–0.00 (m, 6H). $^{13}C\{^1H\}$ ($C_6D_6$): 149.07, 147.0 124.39, 123.98, 123.78, 120.92, 105.22, 50.86, 49.49, 42.80 (m), 34.13, 25.43, 11.0–8.0 (m), 0.0–3.0) (m).

C) 1,1'-(1,2-Ethanediyl)bis(N-(1,1-dimethylethyl)-1-methyl-1-(3-(1-pyrrolidinyl)-1H-inden-1-yl)$^{-2}$, (deloc-1,2, 3,3a,7a:1',2',3',3'a,7'a)-silanamine, Dilithium, Dilithium Salt To a stirred solution of 1,6-bis((N-(tert-butyl)-1-methyl-1-(3-(1-pyrrolidinyl)-1H-inden-1-yl)silanamine))ethane (2.7 g, 4.31 mmol) in 50 mL of toluene was added n-BuLi (11.3 ml, 1.6 M, 18.1 mmol) over fifteen minutes. The original red solution slowly turned to a orange-yellow suspension over one hour. After 16 hours, the yellow/orange suspension was filtered and washed with toluene until the washings became colorless (4×5 mL washes). The sample was then washed 3 times with 20 mL of hexanes and dried in vacuo for 5 hours to leave 2.60 g (93 percent yield) of 1,6-bis((N-(tert-butyl)-1-methyl-1-(3-(1-pyrrolidinyl)-1H-inden-1-yl)silanamine))ethane, tetralithium salt as a fine yellow powder.

D) ($\mu$-((1,1'-(1,2-Ethanediyl)bis(N-(1,1-dimethylethyl)-1-methyl-1-((1,2,3,3a,7a-$\eta$)-3-(1-pyrrolidinyl)-1H-inden-1-yl)silanaminato-$\kappa$N)(4-))))tetrachlorodititanium To a precooled ($-30°$ C.) suspension of $TiCl_3(THF)_3$ (1.27 g, 3.44 mmol) in 20 mL of THF was added a precooled ($-30°$ C.) 20 mL THF solution of 1,6-bis((N-(tert-butyl)-1-methyl-1-(3-(1-pyrrolidinyl)-1H-inden-1-yl)silanamine)) ethane, tetralithium salt (1.12 g, 1.72 mmol). Immediately the color changed to very dark blue/green. After stirring at room temperature for 1 hour, $PbCl_2$ (0.67 g, 2.4 mmol)was added. The color gradually changed to dark blue/purple as lead particles formed. After 1 hour, the volatiles were removed in vacuo and the residue dried in vacuo for 1 hour. The product was extracted into 60 mL of toluene, filtered and the volatiles removed in vacuo. After drying the dark residue in vacuo for an hour, hexanes (20 mL) was added and the dark solid triturated. The volatiles were removed in vacuo, 20 mL of hexanes were added and the solid triturated again. The resulting purple/black suspension was filtered and the solid washed twice with 3 mL of hexanes and dried in vacuo overnight to leave 1.35 g (91 percent yield) of the desired product as a dark purple solid.

$^1$H NMR ($C_6D_6$): 7.80–7.55 (m, 4H), 7.30–6.70 (m, 4H), 5.75 (m, 2H), 3.75–3.00 (m, 4H), 1.45 (br s, 36 H), 1.90–0.50 (m, 15 H). $^{13}C\{^1H\}$ ($C_6D_6$): 149 (m), 136.4, 135.5, 129.5, 129.3, 129.1, 127.4, 126.6, 126.4, 126.1, 106.1 (m), 92.4, 61.1, 50.7, 33.3, 25.9, 15-9 (m), 0.92/0.81/−1.19 (isomers).

Preparation 4
($\mu$-((1,1'-(1,2-Ethanediyl)bis(N-(1,1-dimethylethyl)-1-methyl-1-((1,2,3,3a,7a-$\eta$)-3-(1-pyrrolidinyl)-1H-inden-1-yl)silanaminato-$\kappa$N)(4-)))tetramethyldititanium

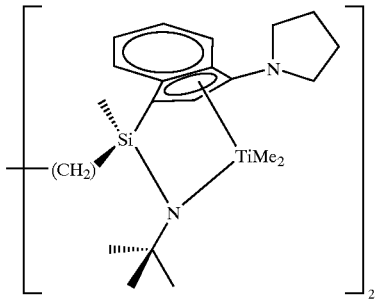

To a suspension of ($\mu$-((1,1'-(1,2-ethanediyl)bis(N-(1,1-dimethylethyl)-1-methyl-1-((1,2,3,3a,7a-$\eta$)-3-(1-pyrrolidinyl)-1H-inden-1-yl)silanaminato-$\kappa$N)(4-)))) tetrachlorodititanium (0.430 g, 0.50 mmol) in 25 mL of diethyl ether was added a solution of MeLi (1.4 $M/Et_2O$, 1.43 mL, 2.00 mmol). Instantly the solution turned dark red. After stirring at room temperature for 1 hour, the volatiles were removed in vacuo and the sample dried in vacuo for 1 hour. The product was extracted into 50 mL of hexanes, the suspension filtered and the brown filter cake washed until no appreciable red color appeared in the washing. The volatiles were removed from the red filtrate and the residue dried in vacuo for 2 hours. The residue was extracted again into hexanes (15 mL) and filtered to remove trace amounts of an insoluble brown residue. The hexanes were removed from the filtrate in vacuo and the resulting red solid dried in vacuo overnight to leave 0.280 g (67 percent yield) of red solid.

$^1$H NMR (C$_6$D$_6$): 7.85–7.45 (m, 4H), 7.10–6.65 (m, 4H), 5.56 (m, 2H), 3.46 (br s, 4H), 3.28 (br m, 4H), 1.55 (sh m, 36H), 1.8–0.50 (m, 12H), 0.09 (m, 6H). $^{13}$C{$^1$H} (C$_6$D$_6$): 144.2 (m), 134.1, 133.8, 126.0–124.0 (m), 104.6 (m), 83.85 (m), 57.89 (m), 54.5 (m), 50.52 (m), 51.0–49.0 (m), 34.99, 26.09, 15.0–10.0 (m), 2.0 (m), −0.40 (m).

Preparation 5
bis(1,1'-(η$^4$-1,3-Butadiene-1,4-diyl)bis(benzene))(μ(1,6-hexanediylbis((methyl-silylidyne)bis((1,2,3,3a,7a-η)-2-methyl-4-phenyl-1H-inden-1-ylidene))))dizirconium

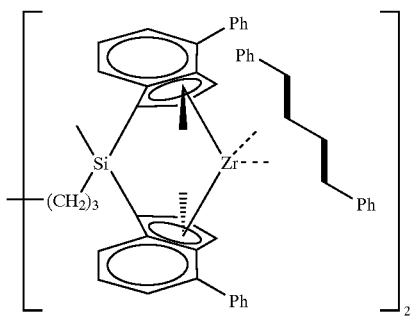

A) Lithium 2-Methyl-4-phenylindenide.

To a solution of 2-methyl-4-phenylindene (10.03 g, 49.3 mmol) in 200 mL of hexanes was added dropwise over 10 minutes 32 mL of 1.6M n-BuLi. The resulting yellow suspension was stirred for 17 hours. The suspension was filtered and the solid washed twice with 5 mL of hexane. The light yellow solid was dried in vacuo for 2 hours to leave 9.21 g (89 percent yield) of lithium 2-methyl-4-phenylindenide. A second crop (0.61 g) was obtained by concentrating the filtrate to about 80 mL and filtering after 4 hours at room temperature. Overall yield was 9.82 g, 95 percent.

B) 1,6-Hexanediylbis(methylbis(2-methyl-4-phenyl-1H-inden-1-yl)-silane

A solution of 1,6-bis(dichloromethylsilyl)hexane (1.78 g, 5.69 mmol) in 20 mL of toluene was added dropwise over 30 minutes to a solution of lithium 2-methyl-4-phenylindenide (5.00 g, 23.9 mmol) in 60 mL of THF. The cloudy orange solution was left to stir at room temperature for 20 hours and then quenched by slow addition of water (80 mL). Most of the THF was removed by rotary evaporation and the product extracted into diethyl ether (120 mL). The organic/aqueous layers were separated and the aqueous layer washed twice with 50 mL of diethyl ether. The organic extracts were combined, dried over MgSO$_4$, filtered and most of the volatiles removed in vacuo. The reaction residue was dissolved in enough toluene to make about 25 mL of a viscous solution. The reaction mixture was subsequently chromatographed on silica (35 cm×5 cm column) initially eluting with hexanes followed by 4:1 hexanes:CH$_2$Cl$_2$ to remove excess 2-methyl-4-phenylindene (Rf=0.62 (silica, 2:1 hexanes:dichloromethane). Further elution with 4:1 hexanes:CH$_2$Cl$_2$ gave one fraction of the desired product 1,6-bis[methylsilyl-bis(2-methyl-4-phenyl-indenyl)hexane (Rf≅0.38 silica, 2:1 hexanes:dichloromethane) which was isolated by removal of volatiles in vacuo to leave 1.53 g (27%) of pale yellow solid. Further elution with 3:1 hexanes:CH$_2$Cl$_2$ led to isolation of a second fraction which has a much broader elution bandwidth (Rf≅0.35–0.10).

Removal of volatiles in vacuo from the sample gave 1.89 g (34 percent) of pale yellow solid. Overall yield was 3.42 g (61 percent).

$^1$H NMR (CDCl$_3$): 7.70–6.9 (m, 32H), 6.74 (m, 4H), 4.0–3.5 (m, 4H), 2.4–1.9 (m, 12H), 1.6–0.4 (m, 12H), 0.45–(−0.2) (m, 6H). $^{13}$C{$^1$H} (CDCl$_3$): 158.2, 150.9, 148.2 (m), 145.9, 143.1 (m), 141.6 (m), 140.55, 137.6, 134.31, 130–120 (several multiplets.), 77.1 (m), 48.9, 47.3 (m), 33.5, 24.1, 18.1 (m), 15.1 (m), 13.2 (m), 12.4 (m), −5.4 (m).

B) 1,6-Hexanediylbis(methylbis(2-methyl-4-phenyl-1H-inden-1-yl)-silane, ion(4-), Tetralithium To a 20 mL toluene solution of 1,6-bis[methylsilyl-bis(2-methyl-4-phenyl-indenyl)hexane (1.01 g, 1.04 mmol) was added n-butyl lithium over 10 minutes (2.7 mL, 1.6 M in hexanes, 4.29 mmol). After 20–30 minutes, a yellow precipitate began to form. After stirring for 18 hours at room temperature, the yellow-orange suspension was filtered and washed twice with 6 mL of toluene then twice with 5 mL of hexane. The sample was dried in vacuo for 5 hours until the weight of sample stabilized to leave 0.91 g (89 percent yield) of tetralithium 1,6-bis[methylsilyl-bis(2-methyl-4-phenyl-indenylide)hexane as a yellow powder.

C) bis(1,1'-(η$^4$-1,3-Butadiene-1,4-diyl)bis(benzene))(μ-(1,6-hexanediylbis((methyl-silylidyne)bis((1,2,3,3a,7a-η)-2-methyl-4-phenyl-1H-inden-1-ylidene))))dizirconium To a −30° C. suspension of tetralithium 1,6-bis [methylsilyl-bis(2-methyl-4-phenyl-indenylide)hexane (0.300 mg, 0.30 mmol) in 5 mL of toluene was added a −30° C. solution of bis(triethylphosphine)(1,4-diphenylbutadiene) zirconium dichloride (0.432 g, 0.60 mmol) in 10 mL of toluene. The reaction was allowed to slowly warm to room temperature as the dark purple/black solution turned red. After stirring overnight, the solution was filtered and the volatiles removed in vacuo. The reaction residue was dissolved in 40 mL of toluene and added dropwise to 60 mL of hexanes. An additional 50 mL of 3:2 hexanes:toluene solvent mixture was added and the resulting orange/brown precipitate filtered and washed extensively with hexanes (3×30 mL). The volatiles were removed from the dark red filtrate and the oily red solid triturated with 10 mL of hexanes and the volatiles removed in vacuo. The trituration was repeated once more with 10 mL of hexanes and the obtained solid was filtered and washed with 5 mL of hexanes. The deep red solid was dried in vacuo overnight to leave 0.306 g (65 percent) of the desired product.

$^1$H NMR (CDCl$_3$): 8.0–7.6 (m, 4H), 7.6–6.6 (m, 52H), 5.6 (br s, 4H), 3.4 (m, 4H), 2.1–0.5 (m, 30H). $^{13}$C{$^1$H} (C$_6$D$_6$): 158.2, 150.9, 148.2 (m), 145.9, 143.1 (m), 141.6 (m), 140.55, 137.6, 134.31, 130–120 (several multiplets.), 77.1 (m), 48.9, 47.3 (m), 33.5, 24.1, 18.1 (m), 15.1 (m), 13.2 (m), 12.4 (m), −5.4 (m).

Polymerizations

A) Ethylene/1-octene Copolymerization

Polymerizations are conducted in a two-liter Parr reactor that is charged with about 740 ml of mixed alkanes solvent and approximately 118 g of 1-octene. Hydrogen, (Δ170 kPa) is added by differential pressure expansion from a 75 mL addition tank. The reactor is charged with ethylene (3.4 MPa) heated to 140° C. and allowed to stabilize. Catalyst and cocatalyst, as solutions in toluene, are premixed in the drybox to give a 1:1 equivalent ratio of catalyst and cocatalyst and charged to the polymerization reactor through a stainless steel transfer line using nitrogen and about 10 ml of a toluene "chaser". The polymerization conditions are maintained for 15 minutes with ethylene on demand. Heat is continuously removed from the reaction through an internal cooling coil. The resulting solution is removed from the reactor, quenched with isopropyl alcohol, and stabilized by addition of a hindered phenol antioxidant (Irganox™ 1010 from Ciba Geigy Corporation). The solvent is removed in a vacuum oven set at 140° C. by heating the polymer solution for about 16 hours. Results are shown in Table 1.

TABLE 1

| Run | Catalyst | Cocatalyst | Efficiency (g polymer/µg Ti) |
|---|---|---|---|
| 1 | TCM[1] | Ex. 3 | 4.4 |
| 2 | " | " | 4.5 |
| 3 | TCD[2] | " | 1.0 |
| 4 | CHEX[3] | " | 0.1 |
| 5 | SiCHEX[4] | " | 0.1 |
| 6 | TCD[2] | Ex. 11 | 0.3 |
| 7 | " | Ex. 12 | 0.9 |
| 8 | " | Ex. 1 | 0.8 |
| 9 | " | Ex. 4 | 0.1 |
| 10 | " | Ex. 5 | 0.4 |
| 11 | " | Ex. 6 | 2.5 |
| 12 | " | Ex. 7 | 0.1 |
| 13 | " | Ex. 9 | 0.2 |
| 14 | " | Ex. 14 | 0.6 |
| 15 | " | Ex. 15 | 1.8 |
| 16 | " | Ex. 16 | 6.3 |

[1](t-butylamido)dimethyl(tetramethylcyclopentadienyl)silanetitanium (IV) dimethyl
[2]((t-butylamido)dimethyl(tetramethylcyclopentadienyl)silanetitanium (II) 1,3-pentadiene
[3][(t-butylamido)dimethyl(4,4-dimethyl-η5-cyclohexadien-1-yl)silane] titanium (IV) dimethyl prepared according to U.S. Pat. No. 5,541,349
[4][(t-butylamido)dimethyl(4,4-dimtehyl-η5-(4-silacyclohexadien-1-yl) silanetitanium (IV) dimethyl prepared analogously to Example 4 of U.S. Pat. No. 5,541,349 using 5,5-dimethyl-5-sila-1,3-cyclohexadiene The forgoing reaction conditions were substantially repeated for comparative purposes using reactor set points of 140° C, and 118 g 1-octene comonomer, run times of 15 minutes, and 0.4 µmoles each of catalyst ((t-butylamido) dimethyl(tetramethylcyclopentadienyl)titanium (II) 1,3-pentadiene) and cocatalyst. The resulting ethylene/1-octene copolymers were analyzed for density and melt index. Results are contained in Table 2.

TABLE 2

| Run | Cocatalyst | Exotherm (° C.) | Yield (g) | Efficiency (g polymer/ µg Ti) | Density (g/ml) | MI[2] |
|---|---|---|---|---|---|---|
| 17 | Example 16 | 8.0 | 176 | 9.2 | 0.897 | 4.5 |
| 18 | " | 2.8 | 156 | 8.1 | 0.900 | 2.8 |
| 19 | " | 7.7 | 188 | 8.8 | 0.899 | 3.2 |
| 20 | " | 9.9 | 175 | 9.2 | 0.899 | 4.1 |
| 21* | MATB[1] | 0.7 | 79 | 4.1 | 0.903 | 1.4 |

*Comparative, not an example of the invention
[1]methylbis(octadecyl)ammonium tetrakis(pentafluorophenyl)borate
[2]Melt index measured by micro melt technique B) Ethylene/styrene Copolymerization Ethylene/styrene copolymerizations were performed in a two-liter Parr reactor that was charged with about 357 g of mixed alkanes solvent and approximately 455 g of styrene. Hydrogen, (Δ350 kPa) was added by differential pressure expansion from a 75 mL addition tank. The reactor was charged with ethylene (1.4 MPa) heated to 90° C. and allowed to stabilize. The desired amount of transition metal component (1 µmole) and cocatalyst as solutions in toluene, were premixed in the drybox to give a 1:1 equivalent ratio of catalyst and cocatalyst and charged to the polymerization reactor through a stainless steel transfer line using nitrogen and about 10 ml of a toluene "chaser". The polymerization conditions were maintained for 15 minutes with ethylene on demand. Heat was continuously removed from the reaction through an internal cooling coil. The resulting solution was removed from the reactor, quenched with isopropyl alcohol, and stabilized by addition of a hindered phenol antioxidant (Irganox™ 1010 from Ciba Geigy Corporation). The solvent was removed in a vacuum oven set at 140° C. by heating the polymer solution for about 16 hours. Results are contained in table 3.

TABLE 3

| Run | Catalyst | Cocatalyst | Efficiency (g polymer/µg Ti or Zr) |
|---|---|---|---|
| 22 | TMC[1] | Ex. 3 | 1.7 |
| 23 | TPI[2] | " | 1.7 |
| 24 | IPH[3] | " | 0.2 |
| 25 | IPE[4] | " | 0.1 |
| 26 | EIZ[5] | " | 2.8 |
| 27 | BHZ[6] | " | 1.3 |

[1](t-butylamido)dimethyl(tetramethylcyclopentadienyl)silanetitanium (II) 1,3-pentadiene
[2](t-butylamido)dimethyl(3-1(1-pyrrolidnyl)inden-1-yl)silanetitanium dimethyl
[3]((µ-((1,1'-hexanediyl)bis(N-(1,1-dimethyl)-1-methyl((1,2,3,3a,7a-η)-3-(1-pyrrolindinyl)-1H-inden-1-yl)silanaminato-κN)(4-))))tetramethylditatanium (preperation 4)
[5]ethylenebis(2-methyl-4-phenylinden-1-yl) zirconium (II) 1,4-diphenylbutadiene
[6]bis(1,1'-(η4-1,3-butadiene-1,4-diyl)bis(benzene))(µ-(1,6-hexandiylbis ((methyl-silylidyne)bis((1,2,3,3a,7a-η)-2-methyl-4-phenyl-1H-inden-1-ylidene))))dizirconium (preperation 5)

C) Propylene Polymerization

Propylene polymerizations were performed in a two-liter, jacketed, Autoclave Engineer's Zipper-Clave™ that was charged with 625 g mixed alkanes solvent and 150 g propylene. Hydrogen, (Δ350 kPa) was added in runs 24, 25 and the control by differential pressure expansion from a 75 mL addition tank. The reactor was heated to the reaction temperature and allowed to stabilize. Ethylenebis(2-methyl-4-phenylinden-1-yl)zirconium (II) 1,4-diphenyl-1,3-butadiene (about 1 µmole) and cocatalyst, as solutions in toluene, were premixed in the drybox to give a 1:1 equivalent ratio of catalyst and cocatalyst and charged to the polymerization reactor through a stainless steel transfer line using nitrogen and a toluene "chaser". The polymerization conditions were maintained for 1 hour or less (depending on the rate of propylene uptake). Heat was continuously removed from the reaction through a cooling coil in the jacket. The resulting solution was removed from the reactor, quenched with isopropyl alcohol, and stabilized by addition of a hindered phenol antioxidant (Irganox™ 1010 from Ciba Geigy Corporation). The solvent was removed in a vacuum oven set at 140° C. by heating the polymer solution for about 16 hours. Results are shown in Table 4.

TABLE 4

| Run | Cocatalyst | T (° C.) | time (min) | Efficiency (g polymer/µg Zr) | Mn[2] |
|---|---|---|---|---|---|
| 28 | Ex. 3 | 70 | 3.6 | 1.19 | — |
| 29 | Ex. 15 | 70 | 3.4 | 1.15 | — |
| 30 | Ex. 16 | 100 | 7.6 | 0.5 | 79,000 |
| 31* | TPB[1] | 70 | 20 | 0.05 | — |

*Comparative, not an example of the invention
[1]Tris(pentafluorophenyl)borane
[2]polymer number average molecular weight

What is claimed is:
1. A catalyst composition comprising:
A) a metal complex corresponding to the formula:

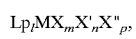

or a dimer thereof, wherein:

Lp is an anionic, delocalized, π-bonded group that is bound to M, containing up to 50 non-hydrogen atoms, optionally two Lp groups may be joined together forming a bridged structure, and further optionally one Lp may be bound to X;

M is a metal of Group 4 of the Periodic Table of the Elements in the +2, +3 or +4 formal oxidation state;

X is an optional, divalent substituent of up to 50 non-hydrogen atoms that together with Lp forms a metallocycle with M;

X' is an optional neutral ligand having up to 20 non-hydrogen atoms;

X" each occurrence is a monovalent, anionic moiety having up to 40 non-hydrogen atoms, optionally, two X" groups may be covalently bound together forming a divalent dianionic moiety having both valences bound to M, or, optionally 2 X" groups may be covalently bound together to form a neutral, conjugated or nonconjugated diene that is π-bonded to M (whereupon M is in the +2 oxidation state), or further optionally one or more X" and one or more X' groups may be bonded together thereby forming a moiety that is both covalently bound to M and coordinated thereto by means of Lewis base functionality;

l is 0, 1 or 2;

m is 0 or 1;

n is a number from 0 to 3;

p is an integer from 0 to 3; and the sum, l+m+p, is equal to the formal oxidation state of M, except when 2 X" groups together form a neutral conjugated or non-conjugated diene that is π-bonded to M, in which case the sum l+m is equal to the formal oxidation state of M; and b) an activator corresponding to the formula:

wherein:

A* is a cation of charge +a, selected from the group consisting of ammonium-, sulfonium-, phosphonium-, oxonium-, carbonium-, silylium-, ferrocenium-, Ag$^+$, and Pb+$^2$;

Z* is an anion group of from 1 to 50 atoms, not counting hydrogen atoms, further containing two or more Lewis base sites and selected from the group consisting of amide and substituted amide, amidinide and substituted amidinide, dicyanamide, imidazolide, substituted imidazolide, imidazolinide, substituted imidazolinide, tricyanomethide, tetracyanoborate, puride, 1,2,3-triazolide, substituted 1,2,3-triazolide, 1,2,4-triazolide, substituted 1,2,4-triazolide, pyrimidinide, substituted pyrimidinide, tetraimidazoylborate and substituted tetraimidazoylborate anions, wherein each substituent, if present, is a $C_{1-20}$ hydrocarbyl, halohydrocarbyl or halocarbyl group, or two such substituents together form a saturated or unsaturated ring system;

J* independently each occurrence is a Lewis acid compound having from 3 to 100 atoms not counting hydrogen coordinated to at least one Lewis base site of Z*, and optionally two or more such J* groups may be joined together in a moiety having multiple Lewis acidic functionality, j is a number from 2 to 12;

a is one; and b, c, and d are integers from 1 to 3, with the proviso that a×b is equal to c×d, or the reaction product thereof.

2. A catalyst composition according to claim 1 wherein the metal complex corresponds to the formula:

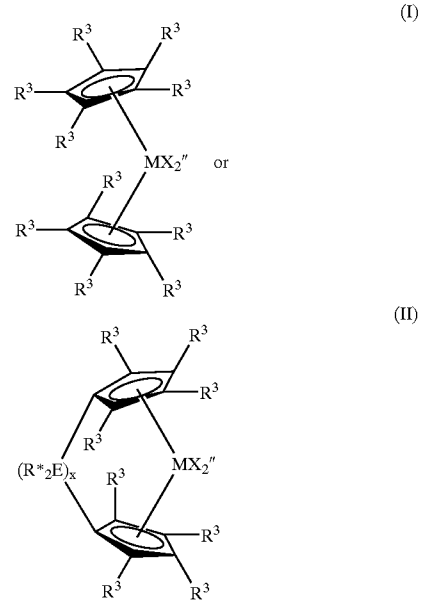

wherein:

M is titanium, zirconium or hafnium, in the +2 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative thereby forming a fused ring system, and X" independently each occurrence is an anionic ligand group of up to 40 non-hydrogen atoms, or two X" groups together form a divalent anionic ligand group of up to non-hydrogen atoms or together are a conjugated diene having from 4 to 30 non-hydrogen atoms forming a π-complex with M, whereupon M is in the +2 formal oxidation state;

E is silicon, germanium, tin, or carbon;

R* independently each occurrence is hydrogen or a group selected from silyl, hydrocarbyl, hydrocarbyloxy and combinations thereof, said R* having up to 30 carbon or silicon atoms; and x is 1 to 8.

3. A catalyst composition according to claim 1 wherein the metal complex corresponds to the corresponds to the formula:

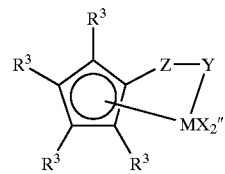

wherein:

M is titanium or zirconium;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative thereby forming a fused ring system, each X" is a halo, hydrocarbyl, hydrocarbyloxy or silyl group, said group having up to 20 non-hydrogen atoms, or two X" groups together form a neutral $C_{5-30}$ conjugated diene or a divalent derivative thereof;

Y is —O—, —S—, —NR*—, —PR*—;

Z is $SiR*_2$, $CR*_2$, $SiR*_2SiR*_2$, $CR*_2CR*_2$, $CR*=CR*$, $CR*_2SiR*_2$, or $GeR*_2$; and R* independently each occurrence is hydrogen or a group selected from silyl, hydrocarbyl, hydrocarbyloxy and combinations thereof, said R* having up to 30 carbon or silicon atoms.

4. A catalyst composition according to any one of claims 1–3 wherein J* corresponds to the formula:

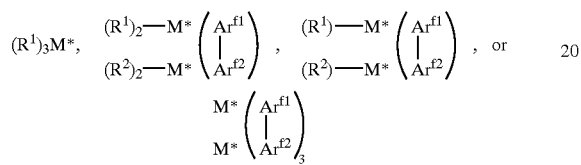

wherein:

M* is aluminum or boron;

$R^1$ and $R^2$ independently each occurrence are hydride, dialkylamido, halide, alkoxide, aryloxide, hydrocarbyl, halocarbyl, or halohydrocarbyl radicals, said $R^1$ or $R^2$ having up to 20 carbons with the proviso that in not more than one occurrence is $R^1$ or $R^2$ halide, and $Ar^{f1}$–$Ar^{f2}$ in combination, independently each occurrence, is a divalent fluoro-substituted aromatic group of from 6 to 20 carbons.

5. A catalyst composition according to claim 4 wherein J* corresponds to the formula: $BR^1_3$ or $AlR^1_3$ wherein: $R^1$ independently each occurrence is a $C_{1-20}$ hydrocarbyl, halocarbyl, or halohydrocarbyl radical.

6. A catalyst composition according to claim 5 wherein $R^1$ is a fluorinated $C_{1-20}$ hydrocarbyl group.

7. A catalyst composition according to claim 6 wherein $R^1$ each occurrence is pentafluorophenyl.

8. A catalyst composition according to any one of claims 1–3 wherein the activator is the tri($C_{1-40}$-alkyl)ammonium salt of bis(tris(pentafluorophenyl)borane)dicyanamide, bis(tris(pentafluorophenyl)borane)imidazolide, bis(tris(pentafluorophenyl)borane)-2-undecylimidazolide, bis(tris(pentafluorophenyl)borane)-5,6-dimethylbenzimidazolide, bis(tris(pentafluorophenyl)borane)-4,5-bis(heptadecyl)imidazolide, tris (tris(pentafluoro-phenyl)boranetricyanomethide, tris(tris(pentafluorophenyl)borane)puride, tetrakis(tris(pentafluorophenyl)borane) tetraimidazoylborate, bis(tris(heptafluoro-2-naphthyl)borane)dicyanamide, bis(tris(heptafluoro-2-naphthyl)borane)imidazolide, bis(tris(heptafluoro-2-naphthyl)borane)-2-undecylimidazolide, bis(tris(heptafluoro-2-naphthyl)borane)-5,6-dimethylbenzimidazolide, bis(tris(heptafluoro-2-naphthyl)borane)-4,5-bis (heptadecyl)imidazolide, tris(tris(heptafluoro-2-naphthyl)boranetricyanomethide, tris(tris(heptafluoro-2-naphthyl)borane)puride, or tetrakis(tris(heptafluoro-2-naphthyl)borane) tetraimidazoylborate.

9. A catalyst composition according to claim 1 wherein the Group 4 metal complex is:

(t-butylamido)dimethyl(tetramethylcyclopentadienyl) titanium dimethyl, (t-butylamido)dimethyl(tetramethylcyclopentadienyl) titanium (II) 1,3-pentadiene, (t-butylamido)dimethyl(tetramethylcyclopentadienyl) titanium (II) 1,4 diphenyl-1,3-butadiene, (cyclohexylamido)dimethyl (tetramethylcyclopentadienyl)titanium dimethyl, cyclohexylamido)dimethyl(tetramethylcyclopentadienyl) titanium (II) 1,3-pentadiene, cyclohexylamido) dimethyl(tetramethylcyclopentadienyl)titanium (II) 1,4 diphenyl-1,3-butadiene, (cyclododecylamido)dimethyl (tetramethylcyclopentadienyl)titanium dimethyl, (cyclododecylamido)dimethyl (tetramethylcyclopentadienyl)titanium (II) 1,3-pentadiene, (cyclododecylamido)dimethyl (tetramethylcyclopentadienyl)titanium (II) 1,4 diphenyl-1,3-butadiene, (t-butylamido)dimethyl(2-methyl-s-indacen-1-yl) titanium dimethyl, (t-butylamido)dimethyl(2-methyl-s-indacen-1-yl) titanium (II) 1,3-pentadiene, (t-butylamido)dimethyl(2-methyl-s-indacen-1-yl) titanium (II) 1,4 diphenyl-1,3-butadiene, (cyclohexylamido)dimethyl(2-methyl-s-indacen-1-yl) titanium dimethyl, cyclohexylamido)dimethyl(2-methyl-s-indacen-1-yl) titanium (II) 1,3-pentadiene, cyclohexylamido)dimethyl(2-methyl-s-indacen-1-yl) titanium (II) 1,4 diphenyl-1,3-butadiene, (cyclododecylamido)dimethyl(2-methyl-s-indacen-1-yl) titanium dimethyl, (cyclododecylamido)dimethyl(2-methyl-s-indacen-1-yl) titanium (II) 1,3-pentadiene, (cyclododecylamido)dimethyl(2-methyl-s-indacen-1-yl) titanium (II) 1,4 diphenyl-1,3-butadiene, (t-butylamido)dimethyl(3,4-(cyclopenta(I)phenanthren-1-yl)titanium dimethyl, (t-butylamido)dimethyl(3,4-(cyclopenta(I)phenanthren-1-yl)titanium (II) 1,3-pentadiene, (t-butylamido)dimethyl(3,4-(cyclopenta(I)phenanthren-1-yl)titanium (II) 1,4 diphenyl-1,3-butadiene, (cyclohexylamido)dimethyl(3,4-(cyclopenta(I) phenanthren-1-yl)titanium dimethyl, cyclohexylamido)dimethyl(3,4-(cyclopenta(I) phenanthren-1-yl)titanium (II) 1,3-pentadiene, cyclohexylamido)dimethyl(3,4-(cyclopenta(I)phenanthren-1-yl)titanium (II) 1,4 diphenyl-1,3-butadiene, (cyclododecylamido)dimethyl(3,4-(cyclopenta(I) phenanthren-1-yl)titanium dimethyl, (cyclododecylamido)dimethyl(3,4-(cyclopenta(I) phenanthren-1-yl)titanium (II) 1,3-pentadiene, (cyclododecylamido)dimethyl(3,4-(cyclopenta(I)phenanthren-1-yl)titanium (II) 1,4 diphenyl-1,3-butadiene,
(t-butylamido)dimethyl(2-methyl-4-phenylinden-1-yl)silanetitanium dimethyl,
(t-butylamido)dimethyl(2-methyl-4-phenylinden-1-yl)silanetitanium(II) 1,3-pentadiene,
(t-butylamido)dimethyl(2-methyl-4-phenylinden-1-yl)silanetitanium(II) 1,4 diphenyl-1,3-butadiene,
(cyclohexylamido)dimethyl(2-methyl-4-phenylinden-1-yl)silanetitanium dimethyl,
cyclohexylamido)dimethyl(2-methyl-4-phenylinden-1-yl)silanetitanium(II) 1,3-pentadiene,
cyclohexylamido)dimethyl(2-methyl-4-phenylinden-1-yl)silanetitanium(II) 1,4 diphenyl-1,3-butadiene,
(cyclododecylamido)dimethyl(2-methyl-4-phenylinden-1-yl)silanetitanium dimethyl,
(cyclododecylamido)dimethyl(2-methyl-4-phenylinden-1-yl)silanetitanium(II) 1,3-pentadiene,
(cyclododecylamido)dimethyl(2-methyl-4-phenylinden-1-yl)silanetitanium(II) 1,4 diphenyl-1,3-butadiene,
(t-butylamido)dimethyl(2-methyl-4-phenylinden-1-yl)silanetitanium dimethyl,
(t-butylamido)dimethyl(2-methyl-4-phenylinden-1-yl)silanetitanium (II) 1,3-pentadiene,
(t-butylamido)dimethyl(2-methyl-4-phenylinden-1-yl)silanetitanium (II) 1,4 diphenyl- 1,3-butadiene,
(cyclohexylamido)dimethyl(2-methyl-4-phenylinden-1-yl)silanetitanium dimethyl,
cyclohexylamido)dimethyl(2-methyl-4-phenylinden-1-yl)silanetitanium(II) 1,3-pentadiene,
cyclohexylamido)dimethyl(2-methyl-4-phenylinden-1-yl)silanetitanium(II) 1,4 diphenyl-1,3-butadiene,
(cyclododecylamido)dimethyl(2-methyl-4-phenylinden-1-yl)silanetitanium dimethyl,
(cyclododecylamido)dimethyl(2-methyl-4-phenylinden-1-yl)silanetitanium(II ) 1,3-pentadiene,
(cyclododecylamido)dimethyl(2-methyl-4-phenylinden-1-yl)silanetitanium(II) 1,4 diphenyl-1,3-butadiene,
(t-butylamido)dimethyl(3-(1-pyrrolidinyl)inden-1-yl)silanetitanium dimethyl,
(t-butylamido)dimethyl(3-(1-pyrrolidinyl)inden-1-yl)silanetitanium(II) 1,3-pentadiene,
(t-butylamido)dimethyl(3-(1-pyrrolidinyl)inden-1-yl)silanetitanium(II) 1,4 diphenyl-1,3-butadiene,
(cyclohexylamido)dimethyl(3-(1-pyrrolidinyl)inden-1-yl)silanetitanium dimethyl,
cyclohexylamido)dimethyl(3-(1-pyrrolidinyl)inden-1-yl)silanetitanium(II) 1,3-pentadiene,
cyclohexylamido)dimethyl(3-(1-pyrrolidinyl)inden-1-yl)silanetitanium(II) 1,4 diphenyl-1,3-butadiene,
(cyclododecylamido)dimethyl(3-(1-pyrrolidinyl)inden-1-yl)silanetitanium dimethyl,
(cyclododecylamido)dimethyl(3-(1-pyrrolidinyl)inden-1-yl)silanetitanium(II) 1,3-pentadiene,
(cyclododecylamido)dimethyl(3-(1-pyrrolidinyl)inden-1-yl)silanetitanium(II) 1,4 diphenyl-1,3-butadiene,
(t-butylamido)dimethyl(3-(1-pyrrolidinyl)inden-1-yl)silanetitanium dimethyl,
(t-butylamido)dimethyl(3-(1-pyrrolidinyl)inden-1-yl)silanetitanium (II) 1,3-pentadiene,
(t-butylamido)dimethyl(3-(1-pyrrolidinyl)inden-1-yl)silanetitanium (II) 1,4 diphenyl-1,3-butadiene,
(cyclohexylamido)dimethyl(3-(1-pyrrolidinyl)inden-1-yl)silanetitanium dimethyl,
cyclohexylamido)dimethyl(3-(1-pyrrolidinyl)inden-1-yl)silanetitanium(II) 1,3-pentadiene,
cyclohexylamido)dimethyl(3-(1-pyrrolidinyl)inden-1-yl)silanetitanium(II) 1,4 diphenyl-1,3-butadiene,
(cyclododecylamido)dimethyl(3-(1-pyrrolidinyl)inden-1-yl)silanetitanium dimethyl,
(cyclododecylamido)dimethyl(3-(1-pyrrolidinyl)inden-1-yl)silanetitanium(II) 1,3-pentadiene,
(cyclododecylamido)dimethyl(3-(1-pyrrolidinyl)inden-1-yl)silanetitanium(II) 1,4 diphenyl-1,3-butadiene,
1,2-ethanebis(inden-1-yl)zirconium dimethyl,
1,2-ethanebis(inden-1-yl)zirconium(II) 1,3-pentadiene,
1,2-ethanebis(inden-1-yl)zirconium(II) 1,4 diphenyl-1,3-butadiene,
1,2-ethanebis(2-methyl-4-phenylinden-1-yl)zirconium dimethyl,
1,2-ethanebis(2-methyl-4-phenylinden-1-yl)zirconium (II) 1,3-pentadiene,
1,2-ethanebis(2-methyl-4-phenylinden-1-yl)zirconium(I) 1,4 diphenyl-1,3-butadiene,
dimethylsilanebis(inden-1-yl)zirconium dimethyl,
dimethylsilanebis(inden-1-yl)zirconium(II) 1,3-pentadiene,
dimethylsilanebis(inden-1-yl)zirconium(II) 1,4 diphenyl-1,3-butadiene,
dimethylsilanebis(2-methyl-4-phenylinden-1-yl)zirconium dimethyl,
dimethylsilanebis(2-methyl-4-phenylinden-1-yl)zirconium(II) 1,3-pentadiene, or
dimethylsilanebis(2-methyl-4-phenylinden-1-yl)zirconium(II) 1,4 diphenyl-1,3-butadiene.

10. A polymerization process comprising contacting one or more olefins under polymerization conditions with a catalyst composition according to any of claims 1–3 .

11. A process according to claim 10 which is a solution polymerization.

12. A polymerization process according to claim 11 which is a continuous solution polymerization.

13. A polymerization process according to claim 10 which is a gas phase polymerization.

* * * * *